US010106583B2

(12) United States Patent
Marozsan et al.

(10) Patent No.: US 10,106,583 B2
(45) Date of Patent: Oct. 23, 2018

(54) MATERIALS AND METHODS FOR PRODUCING CLEAVED, HIV-1 ENVELOPE GLYCOPROTEIN TRIMERS

(71) Applicant: Cornell University, Ithaca, NY (US)

(72) Inventors: Andre Marozsan, Milford, CT (US); Albert Cupo, Stamford, CT (US); John Moore, New York, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 0 days.

(21) Appl. No.: 15/124,306

(22) PCT Filed: Mar. 9, 2015

(86) PCT No.: PCT/US2015/019486
§ 371 (c)(1),
(2) Date: Sep. 7, 2016

(87) PCT Pub. No.: WO2015/134982
PCT Pub. Date: Sep. 11, 2015

(65) Prior Publication Data
US 2017/0015711 A1    Jan. 19, 2017

Related U.S. Application Data

(60) Provisional application No. 61/949,742, filed on Mar. 7, 2014.

(51) Int. Cl.
C12N 15/86 (2006.01)
C12N 5/00 (2006.01)
C07K 14/05 (2006.01)
C07K 14/005 (2006.01)
A61K 39/12 (2006.01)
A61K 39/00 (2006.01)

(52) U.S. Cl.
CPC ............ C07K 14/005 (2013.01); A61K 39/12 (2013.01); C12N 15/86 (2013.01); A61K 39/00 (2013.01); C12N 2740/16122 (2013.01); C12N 2740/16134 (2013.01)

(58) Field of Classification Search
None
See application file for complete search history.

(56) References Cited

U.S. PATENT DOCUMENTS

| | | | |
|---|---|---|---|
| 5,168,062 A | 12/1992 | Stinski | |
| 5,385,839 A | 1/1995 | Stinski | |
| 5,464,758 A | 11/1995 | Gossen et al. | |
| 5,814,618 A | 9/1998 | Bujard et al. | |
| 7,112,715 B2 | 9/2006 | Chambon et al. | |
| 2004/0077577 A1* | 4/2004 | Pavlakis | A61K 39/12 514/44 R |
| 2010/0266635 A1* | 10/2010 | Hanke | A61K 39/21 424/208.1 |
| 2014/0212458 A1* | 7/2014 | Caulfield | A61K 39/21 424/400 |

OTHER PUBLICATIONS

Binley et al. J Virol. 2000, vol. 74(2), pp. 627-643 entitled "A Recombinant Human Immunodeficiency Virus Type 1 Envelope Glycoprotein Complex Stabilized by an Intermolecular Disulfide Bond betwee the gp120 and gp41 Subunits Is an Antigenic Mimic of the Trimeric Virion-Associated Structure." (2000).*
Sanders et al "A nNext-Generation Cleaved, Soluble HIV-1 Env Trimer, BG5O5 SOSIP.664 gp 140, Expresses Multiple Epitopes for BroadlyNeutralizing but Not Non-Neutralizing Antibodies" (PLoS Pathog. September 2013, Vol. 9, No. 9) (2013).*
Pugach et al "A Native-Like SOSIP.664 Trimer Based on an HIV-1 Subtype B env Gene" (Journal of Virology Mar. 2015, vol. 89, No. 6, pp. 3380-3395) (2015).*
Score resuit showing US2014/0212458 (U.S. Appl. No. 14/072209) has 100% identity to instant SEQ No. 21 (May 4, 2017 Score result)*
Aggarwal, Controlling Host-Cell Based Proteolytic Activity in Cho Cultures, *Abstr. Cell Cul. Eng. XIV Conf.*, abstract, D015 (2014).
Berman et al., Protection of chimpanzees from infection by HIV-1 after vaccination with recombinant glycoprotein gp120 but not gp 160, *Nature*, 345:622-625 (1990).
Binley et al., A Recombinant Human Immunodeficiency Virus Type 1 Envelope Glycoprotein Complex Stabilized by an Intermolecular Disulfide Bond between the gp120 and gp41 Subunits Is an Antigenic Mimic of the Trimeric Virion-Associated Structure, *Journal of Virology*, 74(2): 627-643 (2000).
Binley et al., Enhancing the Proteolytic Maturation of Human Immunodeficiency Virus Type 1 Envelope Glycoproteins, *Journal of Virology*, 76(6): 2606-2616 (2002).
Burton et al., HIV vaccine design and the neutralizing antibody problem, *Nature Immunology*, 5(3): 233-236 (2004).
Clements et al., The V3 Loops of the HIV-1 and HIV-2 Surface Glycoproteins Contain Proteolytic Cleavage Sites: A Possible Function in Viral Fusion?, *AIDS Research and Human Retroviruses*, 7(1): 3-16 (1991).
Du et al., Inhibition of V3-specific cleavage of recombinant HIV-1 gp120 produced in Chinese hamster ovary cells, *Protein Expression and Purification*, 59: 223-231 (2008).
Gronostajski et al., Determination of DNA Sequences Essential for FLP-mediated Recombination by Novel Method, *The Journal of Biological Chemistry*, 260(22): 12320-12327 (1985).
Guttman et al., A Functional Interaction between gp41 and gp120 Is Observed for Monomeric but Not Oligomeric, Uncleaved HIV-1 Env gp140, *Journal of Virology*, 87(21): 11462-11475 (2013).
Hallenberger et al., Inhibition of furin-mediated cleavage activation of HIV-1 glycoprotein gp160, *Nature*, 360(6402): 358-361 (1992).

(Continued)

Primary Examiner — Catherine S Hibbert
(74) Attorney, Agent, or Firm — Leydig, Voit & Mayer, Ltd.

(57) ABSTRACT

Expression vectors and mammalian cell lines containing them are described that enable the recombinant production of HIV-1 envelope proteins, including SOSIP modified gp140 trimers capable of inducing broadly neutralizing antibodies.

16 Claims, 22 Drawing Sheets
Specification includes a Sequence Listing.

(56) References Cited

OTHER PUBLICATIONS

Harlow et al., Antibodies, A Laboratory Manual, Second Edition, Cold Spring Harbor Laboratory Press, Cold Spring Harbor, NY (1988) (Table of Contents Only).

Hoffenberg et al., Identification of an HIV-1 Clade A Envelope That Exhibits Broad Antigenicity and Neutralization Sensitivity and Elicits Antibodies Targeting Three Distinct Epitopes, *Journal of Virology*, 87(10): 5372-5383 (2013).

Indra et al., Temporarily-controlled site-specific mutagenesis in the basal layer of the epidermis: comparison of the recombinase activity of the tamoxifen-inducible Cre-Er$^T$ and Cre-ER$^{T2}$ recombinases, *Nucleic Acids Research*, 27(22): 4324-4327 (1999).

Invitrogen by Life Technologies, Growth and Maintenance of Flp-In™ Cell Lines, Instruction Manual, Rev. 3, Invitrogen (2013).

Invitrogen by Life Technologies, pcDNA™5/FRT Vector, Instruction Manual, Invitrogen (2012).

Jayaram, Two-micrometer circle site-specific recombination: The minimal substrate and the possible role of flanking sequences, *Proc. Natl. Acad. Sci. USA*, 82: 5875-5879 (1985).

Julien et al., Crystal Structure of a Soluble Cleaved HIV-1 Envelope Trimer, *Science*, 342: 1477-1483 (2013).

Julien et al., Asymmetric recognition of the HIV-1 trimer by broadly neutralizing antibody PG9, *Proc. Natl. Acad. Sci. U.S.A*, 110(11): 4351-4356 (2013).

Khayat et al., Structural Characterization of Cleaved, Soluble HIV-1 Envelope Glycoprotein Trimers, *Journal of Virology*, 87(17): 9865-9872 (2013).

Kirschner et al., The production of cleaved, trimeric human immunodeficiency virus type 1 (HIV-1) envelope glycoprotein vaccine antigens and infectious pseudoviruses using linear polyethylenimine as a transfection reagent, *Protein Expression and Purification*, 48: 61-68 (2006).

Klasse et al., Influences on Trimerization and Aggregation of Soluble, Cleaved HIV-1 SOSIP Envelope Glycoprotein, *Journal of Virology*, 87(17): 9873-9885 (2013).

Kovacs et al., HIV-1 envelope trimer elicits more potent neutralizing antibody responses than monomeric gp120, *Proc. Natl. Acad. Sci. U.S.A.*, 109(30): 12111-12116 (2012).

Kramer et al., Transgene Control Engineering in Mammalian Cells, *Methods in Molecular Biology*, 308: 123-144 (2005).

Liu et al., Molecular architecture of native HIV-1 gp120 trimers, *Nature*, 455: 109-113 (2008).

Lyumkis et al., Cryo-EM Structure of a Fully Glycosylated Soluble Cleaved HIV-1 Envelope Trimer, *Science*, 342: 1484-1490 (2013).

No et al., Ecdysone-inducible gene expression in mammalian cells and transgenic mice, *Proc. Natl. Acad. Sci. USA*, 93: 3346-3351 (1996).

Pugach et al., A Native-Like SOSIP.664 Trimer Based on an HIV-1 Subtype B env Gene, *Journal of Virology*, 89(6): 3380-3395 (2015).

Ringe et al., Cleavage strongly influences whether soluble HIV-1 envelope glycoprotein trimers adopt a native-like conformation, *Proc. Natl. Acad. Sci. U.S.A.*, 110(45): 18256-18261 (2013).

Sambrook et al., Molecular Cloning: A Laboratory Manual, Fourth Edition, Cold Spring Harbor Press, Cold Spring Harbor, NY, (2001) (Table of Contents only).

Sanders et al., Stabilization of the Soluble, Cleaved, Trimeric Form of the Envelope Glycoprotein Complex of Human Immunodeficiency Virus Type 1, *Journal of Virology*, 76(17): 8875-8889 (2002).

Sanders et al., A Next-Generation Cleaved, Soluble HIV-1 Env Trimer, BG505 SOSIP.664 gp140, Expresses Multiple Epitopes for Broadly Neutralizing but Not Non-Neutralizing Antibodies, *PLoS Pathogens*, 9(9): 1-20 (2013).

Sauer, Site-specific recombination: developments and applications, *Current Opinion in Biotechnology*, 5: 521-27 (1994).

Schulke et al., Oligomeric and Conformational Properties of a Proteolytically Mature, Disulfide-Stabilized Human Immunodeficiency Virus Type 1 gp140 Envelope Glycoprotein, *Journal of Virology*, 76(15): 7760-7776 (2002).

Schulz et al., Effect of Mutations in the V3 Loop of HIV-1 gpl20 on Infectivity and Susceptibility to Proteolytic Cleavage, *AIDS Research and Human Retroviruses*, 9(2):159-166 (1993).

Sellhorn et al., Improving the expression of recombinant soluble HIV Envelope glycoproteins using pseudo-stable transient transfection, *Vaccine*, 28: 430-436 (2010).

Senecoff et al., The FLP recombinase of the yeast 2-nxm plasmid: Characterization of its recombination site, *Proc. Natl. Acad. Sci. USA*, 82: 7270-7274 (1985).

Wagner et al., Nucleotide sequence of the thymidine kinase gene of herpes simplex virus type 1, *Proc. Natl. Acad. Sci. USA*, 78(3): 1441-1445 (1981).

Walker et al., Rational antibody-based HIV-1 vaccine design: current approaches and future directions, *Current Opinion in Immunology*, 22: 358-366 (2010).

Walker et al., Broad neutralization coverage of HIV by multiple highly potent antibodies, *Nature*, 477: 466-470 (2011).

Wilen et al., Phenotypic and Immunologic Comparison of Clade B Transmitted/Founder and Chronic HIV-1 Envelope Glycoproteins, *Journal of Virology*, 85: 8514-8527 (2011).

Wu et al., Neutralization Escape Variants of Human Immunodeficiency Virus Type 1 Are Transmitted from Mother to Infant, *Journal of Virology*, 80(2): 835-844 (2006).

Yasmeen et al., Differential binding of neutralizing and non-neutralizing antibodies to native-like soluble HIV-1 Env trimers, uncleaved Env proteins, and monomeric subunits, *Retrovirology*, 11(41): 1-17 (2014).

Zwick et al., HIV-1 Neutralization: Mechanisms and Relevance to Vaccine Design, *Current HIV Research*, 5: 608-624 (2007).

Chung et al., "Stable 293 T and CHO cell lines expressing cleaved, stable HIV-1 envelope glycoprotein trimers for structural and vaccinal studies", *Retrovirology*, 11(33): 1-14 (2014).

Qin et al., Systematic Comparison of Constitutive Promoters and the Doxycycline-Inducible Promoter, *PLoS One*, 5(5): 1-4 (2010).

GenBank Accession Record No. EU576114.1 dated May 19, 2008.

WIPO, PCT International Search Report and Written Opinion in Application No. PCT/US15/19486 dated Jul. 23, 2015, 16 pages.

\* cited by examiner

Fig. 5

2G12-purified BG505 SOSIP.664 Envelope Protein

|  | 293T | | CHO | |
|---|---|---|---|---|
| M | Transient | Stable | Transient | Stable |

669 kD — trimer
440 kD — dimer
— monomer

BN-PAGE Coomassie stain

SEQUENCE LISTING

```
<160> NUMBER OF SEQ ID NOS: 10

<210> SEQ ID NO 1
<211> LENGTH: 669
<212> TYPE: PRT
<213> ORGANISM: Artificial Sequence
<220> FEATURE:
<223> OTHER INFORMATION: Synthetic

<400> SEQUENCE: 1

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ala Glu Asn Leu Trp Val Thr Val Tyr Tyr Gly Val Pro
        35                  40                  45

Val Trp Lys Asp Ala Glu Thr Thr Leu Phe Cys Ala Ser Asp Ala Lys
    50                  55                  60

Ala Tyr Glu Thr Glu Lys His Asn Val Trp Ala Thr His Ala Cys Val
65                  70                  75                  80

Pro Thr Asp Pro Asn Pro Gln Glu Ile His Leu Glu Asn Val Thr Glu
                85                  90                  95

Glu Phe Asn Met Trp Lys Asn Asn Met Val Glu Gln Met His Thr Asp
            100                 105                 110

Ile Ile Ser Leu Trp Asp Gln Ser Leu Lys Pro Cys Val Lys Leu Thr
        115                 120                 125

Pro Leu Cys Val Thr Leu Gln Cys Thr Asn Val Thr Asn Asn Ile Thr
    130                 135                 140

Asp Asp Met Arg Gly Glu Leu Lys Asn Cys Ser Phe Asn Met Thr Thr
145                 150                 155                 160

Glu Leu Arg Asp Lys Lys Gln Lys Val Tyr Ser Leu Phe Tyr Arg Leu
                165                 170                 175

Asp Val Val Gln Ile Asn Glu Asn Gln Gly Asn Arg Ser Asn Asn Ser
            180                 185                 190

Asn Lys Glu Tyr Arg Leu Ile Asn Cys Asn Thr Ser Ala Ile Thr Gln
        195                 200                 205

Ala Cys Pro Lys Val Ser Phe Glu Pro Ile Pro Ile His Tyr Cys Ala
    210                 215                 220

Pro Ala Gly Phe Ala Ile Leu Lys Cys Lys Asp Lys Lys Phe Asn Gly
225                 230                 235                 240

Thr Gly Pro Cys Pro Ser Val Ser Thr Val Gln Cys Thr His Gly Ile
                245                 250                 255

Lys Pro Val Val Ser Thr Gln Leu Leu Leu Asn Gly Ser Leu Ala Glu
            260                 265                 270

Glu Glu Val Met Ile Arg Ser Glu Asn Ile Thr Asn Asn Ala Lys Asn
        275                 280                 285

Ile Leu Val Gln Phe Asn Thr Pro Val Gln Ile Asn Cys Thr Arg Pro
```

```
            290                 295                 300
Asn Asn Asn Thr Arg Lys Ser Ile Arg Ile Gly Pro Gly Gln Ala Phe
305                 310                 315                 320

Tyr Ala Thr Gly Asp Ile Ile Gly Asp Ile Arg Gln Ala His Cys Asn
                325                 330                 335

Val Ser Lys Ala Thr Trp Asn Glu Thr Leu Gly Lys Val Val Lys Gln
                340                 345                 350

Leu Arg Lys His Phe Gly Asn Asn Thr Ile Ile Arg Phe Ala Asn Ser
                355                 360                 365

Ser Gly Gly Asp Leu Glu Val Thr Thr His Ser Phe Asn Cys Gly Gly
                370                 375                 380

Glu Phe Phe Tyr Cys Asn Thr Ser Gly Leu Phe Asn Ser Thr Trp Ile
385                 390                 395                 400

Ser Asn Thr Ser Val Gln Gly Ser Asn Ser Thr Gly Ser Asn Asp Ser
                405                 410                 415

Ile Thr Leu Pro Cys Arg Ile Lys Gln Ile Ile Asn Met Trp Gln Arg
                420                 425                 430

Ile Gly Gln Ala Met Tyr Ala Pro Pro Ile Gln Gly Val Ile Arg Cys
                435                 440                 445

Val Ser Asn Ile Thr Gly Leu Ile Leu Thr Arg Asp Gly Gly Ser Thr
                450                 455                 460

Asn Ser Thr Thr Glu Thr Phe Arg Pro Gly Gly Gly Asp Met Arg Asp
465                 470                 475                 480

Asn Trp Arg Ser Glu Leu Tyr Lys Tyr Lys Val Val Lys Ile Glu Pro
                485                 490                 495

Leu Gly Val Ala Pro Thr Arg Cys Lys Arg Arg Val Val Gly Arg Arg
                500                 505                 510

Arg Arg Arg Arg Ala Val Gly Ile Gly Ala Val Phe Leu Gly Phe Leu
                515                 520                 525

Gly Ala Ala Gly Ser Thr Met Gly Ala Ala Ser Met Thr Leu Thr Val
                530                 535                 540

Gln Ala Arg Asn Leu Leu Ser Gly Ile Val Gln Gln Gln Ser Asn Leu
545                 550                 555                 560

Leu Arg Ala Pro Glu Ala Gln Gln His Leu Leu Lys Leu Thr Val Trp
                565                 570                 575

Gly Ile Lys Gln Leu Gln Ala Arg Val Leu Ala Val Glu Arg Tyr Leu
                580                 585                 590

Arg Asp Gln Gln Leu Leu Gly Ile Trp Gly Cys Ser Gly Lys Leu Ile
                595                 600                 605

Cys Cys Thr Asn Val Pro Trp Asn Ser Ser Trp Ser Asn Arg Asn Leu
610                 615                 620

Ser Glu Ile Trp Asp Asn Met Thr Trp Leu Trp Asp Lys Glu Ile
625                 630                 635                 640

Ser Asn Tyr Thr Gln Ile Ile Tyr Gly Leu Leu Glu Glu Ser Gln Asn
                645                 650                 655

Gln Gln Glu Lys Asn Glu Gln Asp Leu Leu Ala Leu Asp
                660                 665
```

<210> SEQ ID NO 2
<211> LENGTH: 2007
<212> TYPE: DNA
<213> ORGANISM: Artificial Sequence
<220> FEATURE:
<223> OTHER INFORMATION: Synthetic

<400> SEQUENCE: 2

```
atggatgcta tgaaacgcgg cctgtgctgc gtactgctgc tgtgtggtgc tgtatttgta      60
tcccccagcc aagagataca tgcacgcttt cggagagggg cacgtgctga aacttatgg     120
gtaacagtat attacggggt accagtatgg aaagacgctg aaactacatt gttttgtgcc    180
tcggatgcta agcatatga cagagaaag cataatgtct gggcgactca cgcatgcgtc      240
cccacggatc caaatcctca agaaatccac ctagagaacg ttaccgaaga attcaatatg    300
tggaaaaaca atatggtaga acagatgcac actgatataa tttctctgtg ggatcaaagt    360
ttaaaaccat gcgttaagct tacccccgctt gcgtcacac ttcagtgcac taacgtcact    420
aataatatca cggacgacat gaggggggaa ctaaaaaatt gttcttttaa tatgacgact    480
gaactcagag acaaaaaaca aaagtgtac tctttattt acaggctgga tgtggtgcaa     540
ataaacgaga tcagggaaa ccgctctaat aattccaaca aagagtatcg attgattaat     600
tgtaatactt cggctattac ccaagcttgt ccgaaagtgt cctttgagcc gatacctatt    660
cattactgtg ctccggctgg ctttgcaatc cttaagtgca aggataagaa gttcaatggg    720
actgggccgt gcccctctgt gtccacggtg caatgtacac acggcatcaa gccagtagtc    780
tctactcaac tgctattgaa cggcagccta gccgaggagg aagtgatgat tagatccgaa    840
aacatcacca ataatgcgaa gaacatcctt gttcagttca atacacccgt ccaaataaat    900
tgcactcgcc caaataataa caccaggaag tcgatccgca ttgggcccgg gcaggctttc    960
tatgccactg gggacataat tggtgacata cggcaggcgc actgtaacgt tagcaaagct    1020
acatggaacg agactctagg taaagtcgtc aagcagctga ggaagcactt cggaaacaac    1080
acaattatcc gatttgcaaa ttcctcgggg ggcgatctgg aggttactac acattctttt    1140
aactgcgggg gcgagttctt ctattgtaac acgagtgggg tgtttaatag cacctggatc    1200
tccaacacat ctgtacaggg ttccaactcc accggatcta atgatagtat aactttacct    1260
tgcaggataa agcaaataat aaatatgtgg cagagaatcg gccaggctat gtacgccccg    1320
cctatacagg gcgtcatcag gtgtgtatct aatatcactg ggttaattct gacacgagat    1380
ggaggttcta ccaatagcac aaccgagacg tttaggccgg ggggtggtga tatgcgcgat    1440
aattggcgat cagaactcta caaatataaa gtggtgaaaa tagaaccact cggagttgcc    1500
ccaacccgat gcaaacggag agtagtgggg agacgtcggc gccgacgtgc ggttggaatt    1560
ggtgccgtgt ttttaggttt tctaggggct gctggatcaa caatgggagc tgcttcaatg    1620
accttgactg tgcaagcaag gaatctcctt tcagggatag tccaacagca gtcaaacctc    1680
cttagagccc cggaagcaca acaacaccta ttgaaattaa ccgtgtgggg gataaagcaa    1740
cttcaagccc gtgtactcgc ggttgaacgg taccttcgcg accaacagct cctagggatt    1800
tggggttgtt cgggcaaatt aatttgttgc acaaatgttc cttggaacag ttcgtggagt    1860
aatcgaaatc tttccgaaat atgggataac atgacatggc ttcaatggga caaagagatc    1920
tccaattata cccaaatcat atatggtctc ctagaagaga gccagaatca acaggaaaaa    1980
aatgaacaag atctccttgc attagac                                        2007
```

<210> SEQ ID NO 3
<211> LENGTH: 677
<212> TYPE: PRT
<213> ORGANISM: Artificial Sequence
<220> FEATURE:
<223> OTHER INFORMATION: Synthetic

<400> SEQUENCE: 3

```
Met Asp Ala Met Lys Arg Gly Leu Cys Cys Val Leu Leu Cys Gly
 1               5                  10                 15

Ala Val Phe Val Ser Pro Ser Gln Glu Ile His Ala Arg Phe Arg Arg
            20                  25                 30

Gly Ala Arg Ala Ala Lys Lys Trp Val Thr Val Tyr Tyr Gly Val Pro
            35                  40                 45

Val Trp Lys Glu Ala Thr Thr Thr Leu Phe Cys Ala Ser Asp Ala Lys
 50                  55                 60

Ala Tyr Asp Thr Glu Val His Asn Val Trp Ala Thr His Ala Cys Val
 65                  70                 75                 80

Pro Thr Asp Pro Asn Pro Gln Glu Ile Val Leu Gly Asn Val Thr Glu
                 85                 90                 95

Asn Phe Asn Met Trp Lys Asn Asn Met Val Glu Gln Met His Glu Asp
                100                105                110

Ile Ile Ser Leu Trp Asp Gln Ser Leu Lys Pro Cys Val Lys Leu Thr
            115                120                125

Pro Leu Cys Val Thr Leu Asn Cys Asn Asn Val Asn Thr Asn Asn Thr
 130                 135                140

Asn Asn Ser Thr Asn Ala Thr Ile Ser Asp Trp Glu Lys Met Glu Thr
 145                 150                155                160

Gly Glu Met Lys Asn Cys Ser Phe Asn Val Thr Thr Ser Ile Arg Asp
                165                170                175

Lys Ile Lys Lys Glu Tyr Ala Leu Phe Tyr Lys Leu Asp Val Val Pro
                180                185                190

Leu Glu Asn Lys Asn Asn Ile Asn Thr Asn Ile Thr Asn Tyr Arg
            195                200                205

Leu Ile Asn Cys Asn Thr Ser Val Ile Thr Gln Ala Cys Pro Lys Val
 210                 215                220

Ser Phe Glu Pro Ile Pro Ile His Tyr Cys Ala Pro Ala Gly Phe Ala
 225                 230                235                240

Ile Leu Lys Cys Asn Ser Lys Thr Phe Asn Gly Ser Gly Pro Cys Thr
                245                250                255

Asn Val Ser Thr Val Gln Cys Thr His Gly Ile Arg Pro Val Val Ser
                260                265                270

Thr Gln Leu Leu Leu Asn Gly Ser Leu Ala Glu Glu Ile Val Ile
            275                280                285

Arg Ser Glu Asn Ile Thr Asp Asn Ala Lys Thr Ile Ile Val Gln Leu
 290                 295                300

Asn Glu Ala Val Glu Ile Asn Cys Thr Arg Pro Asn Asn Asn Thr Arg
 305                 310                315                320

Lys Ser Ile His Ile Gly Pro Gly Arg Ala Phe Tyr Ala Thr Gly Asp
                325                330                335

Ile Ile Gly Asn Ile Arg Gln Ala His Cys Asn Ile Ser Lys Ala Arg
                340                345                350

Trp Asn Glu Thr Leu Gly Gln Ile Val Ala Lys Leu Glu Glu Gln Phe
                355                360                365

Pro Asn Lys Thr Ile Ile Phe Asn His Ser Ser Gly Gly Asp Pro Glu
                370                375                380

Ile Val Thr His Ser Phe Asn Cys Gly Gly Glu Phe Phe Tyr Cys Asn
 385                 390                395                400

Thr Thr Pro Leu Phe Asn Ser Thr Trp Asn Asn Thr Arg Thr Asp Asp
                405                410                415
```

```
Tyr Pro Thr Gly Gly Glu Gln Asn Ile Thr Leu Gln Cys Arg Ile Lys
                420                 425                 430

Gln Ile Ile Asn Met Trp Gln Gly Val Gly Lys Ala Met Tyr Ala Pro
        435                 440                 445

Pro Ile Arg Gly Gln Ile Arg Cys Ser Ser Asn Ile Thr Gly Leu Leu
    450                 455                 460

Leu Thr Arg Asp Gly Arg Asp Gln Asn Gly Thr Glu Thr Phe Arg
465                 470                 475                 480

Pro Gly Gly Gly Asn Met Arg Asp Asn Trp Arg Ser Glu Leu Tyr Lys
                485                 490                 495

Tyr Lys Val Val Lys Ile Glu Pro Leu Gly Ile Ala Pro Thr Ala Cys
            500                 505                 510

Lys Arg Arg Val Val Gln Arg Arg Arg Arg Ala Val Gly Leu
            515                 520                 525

Gly Ala Phe Ile Leu Gly Phe Leu Gly Ala Ala Gly Ser Thr Met Gly
    530                 535                 540

Ala Ala Ser Met Ala Leu Thr Val Gln Ala Arg Leu Leu Leu Ser Gly
545                 550                 555                 560

Ile Val Gln Gln Gln Asn Asn Leu Leu Arg Ala Pro Glu Ala Gln Gln
                565                 570                 575

His Met Leu Gln Leu Thr Val Trp Gly Ile Lys Gln Leu Gln Ala Arg
            580                 585                 590

Val Leu Ala Val Glu Arg Tyr Leu Arg Asp Gln Gln Leu Leu Gly Ile
        595                 600                 605

Trp Gly Cys Ser Gly Lys Ile Ile Cys Cys Thr Asn Val Pro Trp Asn
    610                 615                 620

Asp Ser Trp Ser Asn Lys Thr Ile Asn Glu Ile Trp Asp Asn Met Thr
625                 630                 635                 640

Trp Met Gln Trp Glu Lys Glu Ile Asp Asn Tyr Thr Gln His Ile Tyr
                645                 650                 655

Thr Leu Leu Glu Val Ser Gln Ile Gln Gln Glu Lys Asn Glu Gln Glu
            660                 665                 670

Leu Leu Glu Leu Asp
        675

<210> SEQ ID NO 4
<211> LENGTH: 2031
<212> TYPE: DNA
<213> ORGANISM: Artificial Sequence
<220> FEATURE:
<223> OTHER INFORMATION: Synthetic

<400> SEQUENCE: 4
atggatgcta tgaaagagg actgtgttgt gtgctgctgc tgtgtggagc tgtgtttgtg      60
tcaccaagcc aggagattca cgcaaggttc cggagaggag cccgggccgc taagaaatgg     120
gtgaccgtct actatggcgt gccagtctgg aaggaggcaa ccacaactct gttttgcgcc     180
tccgacgcca aggcctacga tacagaagtg cacaacgtct gggctaccca tgcatgtgtg     240
cccacagatc caaaccccca ggagatcgtg ctggggaatg tcaccgaaaa tttcaacatg     300
tggaagaaca atatggtgga gcagatgcac gaagacatca tttccctgtg ggatcagtct     360
ctgaagccat gcgtgaagct acacccctg tgcgtcactc tgaattgtaa caacgtgaac     420
actaacaaca ccaacaatag tacaaacgcc actatctcag actgggaaaa gatggagacc     480
ggcgaaatga aaaattgtag cttcaacgtg accacatcca tccgggataa aattaagaaa     540
```

```
gagtacgccc tgttttataa gctggatgtg gtcccctgg aaaacaaaaa caacatcaac    600
aacaccaaca ttacaaacta cagactgatc aattgcaaca cgtccgtcat acccaggcc    660
tgtcccaagg tgtcattcga gcctatccca attcactatt gcgcacctgc cggcttcgct    720
atcctgaagt gtaactctaa gactttaac ggaagtggcc cttgcacaaa cgtgagcact    780
gtccagtgta cccatgggat caggccagtg gtctccacac agctgctgct gaatggatct    840
ctggccgagg aagagatcgt gattcgctcc gagaatatca ccgataacgc caaaacaatc    900
attgtgcagc tgaatgaggc tgtcgaaatt aactgcactc gccctaacaa taacacccga    960
aagtctatcc acattgggcc aggaagagcc ttttacgcta ccggggacat cattggaaat   1020
atccggcagg ctcattgtaa cattagtaag gcaagatgga atgagacact gggccagatc   1080
gtggccaagc tggaagagca gttcccaaac aagacaatca ttttaaccag cagctccggc   1140
ggcgaccccg agattgtgac tcatagcttc aactgcggag gcgaattctt ttactgtaat   1200
actaccccc tgtttaactc cacctggaat aacacacgaa ctgacgatta tcctacaggg   1260
ggagagcaga acatcactct ccagtgcaga attaagcaga tcattaatat gtggcagggc   1320
gtggggaaag caatgtatgc cccccctatc aggggccaga ttcgctgttc tagtaacatc   1380
actggactgc tgctgacccg agacggcggg cgggatcaga atggaaccga aaccttccgg   1440
cctggaggcg gaatatgag agacaactgg aggagcgagc tgtacaagta taaagtggtc   1500
aagatcgaac ccctgggcat tgctcctacc gcatgcaaaa ggcgcgtggt ccagcgacga   1560
agaaggcggc gcgccgtggg actgggagca ttcatcctgg ggtttctggg agcagccggc   1620
tcaaccatgg gagctgcaag catggccctg acagtccagg ctaggctgct gctgtctggg   1680
atcgtgcagc agcagaataa cctgctgcga gcacctgagg ctcagcagca catgctccag   1740
ctgaccgtgt ggggcatcaa gcagctccag gcacgagtgc tggcagtcga acggtacctg   1800
agagatcagc agctgctggg gatttgggga tgcagcggca agatcatttg ctgtacaaat   1860
gtgccatgga acgactcatg gagcaacaag actatcaacg agatttggga taacatgacc   1920
tggatgcagt gggaaaagga gatcgacaat tacacacagc atatctacac tctgctggaa   1980
gtgtcacaga ttcagcagga gaagaacgaa caggaactgc tggaactgga t            2031
```

<210> SEQ ID NO 5
<211> LENGTH: 687
<212> TYPE: PRT
<213> ORGANISM: Artificial Sequence
<220> FEATURE:
<223> OTHER INFORMATION: Synthetic

<400> SEQUENCE: 5

Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg Arg
            20                  25                  30

Gly Ala Arg Met Glu Gln Leu Trp Val Thr Val Tyr Tyr Gly Val Pro
        35                  40                  45

Val Trp Lys Glu Ala Lys Ala Thr Leu Phe Cys Ala Ser Asp Ala Lys
    50                  55                  60

Ala Tyr Glu Lys Glu Val His Asn Val Trp Ala Thr His Ala Cys Val
65                  70                  75                  80

Pro Thr Asp Pro Asn Pro Gln Glu Ile Pro Leu Gly Asn Val Thr Glu
                85                  90                  95

Asn Phe Asn Met Trp Lys Asn Asp Met Ala Asp Gln Met His Glu Asp

-continued

```
                100                 105                 110
    Ile Ile Ser Leu Trp Asp Gln Ser Leu Lys Pro Cys Val Lys Leu Thr
                115                 120                 125

Pro Leu Cys Val Thr Leu Asn Cys Ser Asp Ala Thr Ser Asn Thr Thr
                130                 135                 140

Lys Asn Ala Thr Asn Thr Asn Thr Thr Ser Thr Asp Asn Arg Asn Ala
    145                 150                 155                 160

Thr Ser Asn Asp Thr Glu Met Lys Gly Glu Ile Lys Asn Cys Thr Phe
                    165                 170                 175

Asn Ile Thr Thr Glu Val Arg Asp Arg Lys Thr Lys Gln Arg Ala Leu
                180                 185                 190

Phe Tyr Lys Leu Asp Val Val Pro Leu Glu Glu Lys Asn Ser Ser
                195                 200                 205

Ser Lys Asn Ser Ser Tyr Lys Glu Tyr Arg Leu Ile Ser Cys Asn Thr
                210                 215                 220

Ser Thr Ile Thr Gln Ala Cys Pro Lys Val Ser Phe Asp Pro Ile Pro
    225                 230                 235                 240

Ile His Tyr Cys Ala Pro Ala Gly Tyr Ala Ile Leu Lys Cys Asn Asn
                    245                 250                 255

Lys Thr Phe Asn Gly Thr Gly Pro Cys His Asn Val Ser Thr Val Gln
                260                 265                 270

Cys Thr His Gly Ile Lys Pro Val Val Ser Thr Gln Leu Leu Leu Asn
                275                 280                 285

Gly Ser Leu Ala Glu Glu Ile Ile Ile Arg Ser Glu Asn Leu Thr
                290                 295                 300

Asp Asn Thr Lys Thr Ile Ile Val His Leu Asn Glu Ser Val Glu Ile
    305                 310                 315                 320

Asn Cys Thr Arg Pro Asn Asn Asn Thr Arg Lys Ser Val Arg Ile Gly
                    325                 330                 335

Pro Gly Gln Thr Phe Phe Ala Thr Gly Glu Ile Ile Gly Asp Ile Arg
                340                 345                 350

Gln Ala His Cys Asn Leu Ser Lys Ser Asn Trp Thr Thr Thr Leu Lys
                355                 360                 365

Arg Ile Glu Lys Lys Leu Lys Glu His Phe Asn Asn Ala Thr Ile Lys
                370                 375                 380

Phe Glu Ser Ser Ala Gly Gly Asp Leu Glu Ile Thr Thr His Ser Phe
    385                 390                 395                 400

Asn Cys Arg Gly Glu Phe Phe Tyr Cys Asn Thr Ser Gly Leu Phe Asn
                    405                 410                 415

Ser Ser Leu Leu Asn Asp Thr Asp Gly Thr Ser Asn Ser Thr Ser Asn
                420                 425                 430

Ala Thr Ile Thr Leu Pro Cys Arg Ile Lys Gln Ile Ile Asn Met Trp
                435                 440                 445

Gln Glu Val Gly Arg Ala Met Tyr Ala Ser Pro Ile Ala Gly Ile Ile
    450                 455                 460

Thr Cys Lys Ser Asn Ile Thr Gly Leu Leu Leu Thr Arg Asp Gly Gly
    465                 470                 475                 480

Asn Lys Ser Ala Gly Ile Glu Thr Phe Arg Pro Gly Gly Gly Asn Met
                    485                 490                 495

Lys Asp Asn Trp Arg Ser Glu Leu Tyr Lys Tyr Lys Val Val Glu Ile
                500                 505                 510

Lys Pro Leu Gly Ile Ala Pro Thr Ser Cys Lys Arg Arg Val Val Glu
                515                 520                 525
```

```
Arg Arg Arg Arg Arg Arg Ala Gly Ile Gly Ala Val Ile Leu Gly
            530                 535                 540
Phe Leu Gly Ala Ala Gly Ser Thr Met Gly Ala Ala Ser Val Met Leu
545                 550                 555                 560
Thr Val Gln Ala Arg Gln Leu Leu Ser Gly Ile Val Gln Gln Gln Ser
                565                 570                 575
Asn Leu Leu Arg Ala Pro Glu Ala Gln Gln His Met Leu Gln Leu Thr
            580                 585                 590
Val Trp Gly Ile Lys Gln Leu Gln Thr Arg Val Leu Ala Ile Glu Arg
            595                 600                 605
Tyr Leu Lys Asp Gln Gln Leu Leu Gly Leu Trp Gly Cys Ser Gly Lys
            610                 615                 620
Leu Ile Cys Cys Thr Ala Val Pro Trp Asn Thr Ser Trp Ser Asn Lys
625                 630                 635                 640
Ser Lys Asp Glu Ile Trp Asp Asn Met Thr Trp Met Gln Trp Asp Arg
                645                 650                 655
Glu Ile Asp Asn Tyr Thr Gln Val Ile Tyr Gln Leu Leu Glu Val Ser
            660                 665                 670
Gln Asn Gln Gln Glu Lys Asn Glu Asn Asp Leu Leu Ala Leu Asp
            675                 680                 685

<210> SEQ ID NO 6
<211> LENGTH: 2064
<212> TYPE: DNA
<213> ORGANISM: Artificial Sequence
<220> FEATURE:
<223> OTHER INFORMATION: Synthetic

<400> SEQUENCE: 6
atggacgcta tgaaacgggg gctgtgctgc gtgctgctgc tgtgcggggc tgtctttgtc      60
tcaccttctc aggaaatcca tgccagattc cggagagggg ccaggatgga gcagctgtgg     120
gtgactgtct actatggagt gcccgtctgg aaggaagcaa agccaccct gttttgcgct      180 tccgacgcta aggcatacga aaaagaggtg cacaatgtct gggcaacaca tgcctgcgtg     240
cccactgatc ccaatcctca ggaaatccct ctgggcaacg tgaccgagaa tttcaacatg     300
tggaagaacg acatggccga tcagatgcac gaggacatca tttccctgtg ggatcagtct     360
ctgaagcctt gcgtgaagct acccccactg tgcgtcacac tgaattgttc tgacgctaca     420
agtaatacca caagaacgc aactaatacc aacactacct ccactgacaa tcggaacgcc      480
acatctaacg atactgaaat gaagggcgag atcaagaatt gtacattcaa catcacaact     540
gaggtgcggg acagaaagac taaacagagg gctctgtttt ataagctgga tgtggtccct     600
ctggaggaag agaagaatag ctcctctaaa aacagttcat acaaggaata tcgcctgatt     660
tcatgcaaca cgtcaactat cacccaggct tgtcctaaag tgagcttcga cccaattccc     720
atccattact gcgccccagc tggctatgca atcctgaagt gtaacaacaa gaccttcaac     780
gggacaggac cctgccacaa cgtgagcact gtccagtgta cccatggcat caagcctgtg     840
gtcagtactc agctgctgct gaacgggtca ctggccgaag aggaaatcat tatccggagc     900
gagaatctga cagataacac aaagactatt atcgtgcacc tgaatgaatc agtcgagatt     960
aactgcacca gaccaaacaa taacacacgc aaaagcgtgc gaatcggccc cgggcagaca    1020
ttctttgcaa ctggggagat tatcggagac attaggcagg ccattgtaa tctgtccaag    1080 tctaactgga ccacaactct gaaacgcatc gaaagaaac tgaaggagca cttcaataac    1140
```

```
gccaccatca agtttgaaag ctccgctggc ggggatctgg agatcaccac acattctttc    1200
aattgccggg gagagttctt ttactgtaac accagtggcc tgtttaattc tagtctgctg    1260
aacgacactg atggcaccag taattcaaca agcaacgcca ccattacact gccatgcagg    1320
atcaagcaga ttatcaacat gtggcaggaa gtggggcgcg ctatgtatgc aagccccatt    1380
gcaggaatta tcacctgtaa atccaatatc actggcctgc tgctgaccag agacggaggc    1440
aacaagtccg ccggaatcga cattccgc caggaggag caatatgaa agataactgg    1500 cgatctgaac tgtacaagta taaagtggtc gagatcaagc cactgggcat cgcccccacc    1560
agttgcaaga ggcgcgtggt cgagcgacgg agaaggcggc gcgccgctgg aattggcgct    1620
gtgatcctgg ggtttctggg agcagccggc tctacaatgg gggctgcaag tgtgatgctg    1680
actgtccagg cccggcagct gctgtcagga atcgtgcagc agcagagcaa cctgctgaga    1740
gcccctgagg ctcagcagca catgctccag ctgaccgtgt ggggcattaa gcagctccag    1800
acaagggtcc tggctatcga acgctacctg aaagaccagc agctgctggg gctgtggga    1860 tgttccggca agctgatctg ctgtaccgcc gtgccatgga atacctcctg gtctaacaag    1920
tctaaagacg aaatctggga taatatgacc tggatgcagt gggacaggga gattgataac    1980
tacacacagg tcatctacca gctgctggaa gtctcccaga atcagcagga aaagaatgag    2040
aacgacctgc tggccctgga ttga                                          2064
```

<210> SEQ ID NO 7
<211> LENGTH: 10894
<212> TYPE: DNA
<213> ORGANISM: Artificial Sequence
<220> FEATURE:
<223> OTHER INFORMATION: Synthetic

<400> SEQUENCE: 7

```
gacggatcgg agatctcccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttatgg acgctatgaa aaggggctg tgctgtgtgc tgctgctgtg    960
cggggctgtg tttgtgtcac ccagtcagga atccacgcc agattccgga gaggagctag    1020
ggcagaaaac ctgtgggtga cagtctacta tggcgtgcct gtctggaagg acgccgagac    1080
cacactgttt tgcgcttccg atgccaaggc ttacgaaact gagaaacaca atgtgtgggc    1140
```

```
tacccatgca tgtgtcccaa cagacccaaa cccccaggaa atccacctgg agaatgtgac    1200
cgaggaattc aacatgtgga agaacaatat ggtggagcag atgcatacag acatcatttc    1260
cctgtgggat cagtctctga agccttgcgt gaaactgacc ccactgtgcg tcacactcca    1320
gtgtacaaac gtgactaaca atatcaccga cgatatgcgc ggagaactga agaattgttc    1380
tttcaacatg actaccgagc tgagggacaa gaaacagaaa gtgtacagtc tgttttatcg    1440
cctggatgtg gtccagatca atgaaaacca ggggaataga agtaacaatt caaacaagga    1500
gtacaggctg atcaattgca acaccagtgc cattacacag gcttgtccaa agtgtcatt    1560 tgaacctatc ccaattcatt attgcgcacc tgccggcttc gccatcctga agtgtaaaga    1620
taagaagttc aacggcactg ggccctgccc ttcagtgagc actgtccagt gtacccacgg    1680
gattaagcct gtggtctcca cccagctgct gctgaatgga tctctggccg aggaagaagt    1740
gatgatccgg tctgagaaca tcactaacaa cgctaagaac atcctggtgc agttcaacac    1800
ccccgtccag attaattgca ctagacctaa caataacacc aggaaatcta tccgcattgg    1860
acccggccag gccttttatg ctaccggcga catcattggg gatatccggc aggcacactg    1920
taatgtgagc aaggctacat ggaacgagac tctggggaag gtggtcaaac agctgcgcaa    1980
acatttcgga aataacacca tcattcgatt tgccaatagc tccggcgggg acctggaagt    2040
gacaactcac agcttcaact gcggaggcga gttcttttac tgtaacacaa gtggcctgtt    2100
taattcaact tggatcagca acacctccgt gcagggatcc aattctaccg gctctaacga    2160
tagtatcaca ctgccatgcc ggattaagca gatcattaat atgtggcaga gaatcgggca    2220
ggcaatgtat gccccccccta tccagggagt gattcgatgt gtcagcaata tcacaggcct    2280
gattctgact agagacgggg gatcaacaaa cagcaccaca gagactttca ggcccggcgg    2340
gggagacatg cgagataact ggcggtccga actgtacaag tataaagtgg tcaagatcga    2400
gccactggga gtggcaccaa cccgatgcaa aaggcgagtg tcggacgac gaagaaggcg    2460 acgagctgtg gggattggag cagtcttcct gggctttctg ggggccgctg atctacaat    2520 gggcgcagcc agtatgactc tgaccgtcca ggccaggaat ctgctgtcag ggatcgtgca    2580
gcagcagagc aacctgctgc gcgctcccga agcacagcag catctgctga agctgaccgt    2640
gtggggcatc aagcagctcc aggcacgagt gctggcagtc gagcggtacc tgagagatca    2700
gcagctgctg ggaatctggg ggtgcagcgg aaagctgatt tgctgtacca atgtgccttg    2760
gaactctagt tggagcaata gaaacctgtc cgaaatctgg gacaatatga catggctcca    2820
gtgggataag gagattagca actacactca gatcatctac ggcctgctgg aagagtccca    2880
gaatcagcag gagaagaacg agcaggacct gctggccctg gattaaaata aaatatcttt    2940
attttcatta catctgtgtg ttggtttttt gtgtgtatgg gagtaattca tacaaaagga    3000
ctcgcccctg ccttggggaa tcccagggac cgtcgttaaa ctcccactaa cgtagaaccc    3060
agagatcgct gcgttcccgc cccctcaccc gcccgctctc gtcatcactg aggtggagaa    3120
gagcatgcgt gaggctccgg tgcccgtcag tgggcagagc gcacatcgcc cacagtcccc    3180
gagaagttgg ggggagggt cggcaattga accggtgcct agagaaggtg gcgcggggta    3240
aactgggaaa gtgatgtcgt gtactggctc cgcctttttc ccgagggtgg gggagaaccg    3300
tatataagtg cagtagtcgc cgtgaacgtt cttttttcgca acgggtttgc cgccagaaca    3360
caggtaagtg ccgtgtgtgg ttcccgcggg cctggcctct ttacgggtta tggcccttgc    3420
gtgccttgaa ttacttccac gcccctggct gcagtacgtg attcttgatc ccgagcttcg    3480
```

```
ggttggaagt gggtgggaga gttcgaggcc ttgcgcttaa ggagcccctt cgcctcgtgc    3540
ttgagttgag gcctggcttg ggcgctgggg ccgccgcgtg cgaatctggt ggcaccttcg    3600
cgcctgtctc gctgctttcg ataagtctct agccatttaa aattttgat gacctgctgc     3660 gacgctttt ttctggcaag atagtcttgt aaatgcgggc caagatctgc acactggtat    3720
ttcggttttt ggggccgcgg gcggcgacgg ggcccgtgcg tcccagcgca catgttcggc    3780 gaggcgggc ctgcgagcgc ggccaccgag aatcggacgg gggtagtctc aagctggccg     3840
gcctgctctg gtgcctggcc tcgcgccgcc gtgtatcgcc ccgccctggg cggcaaggct    3900
ggcccggtcg gcaccagttg cgtgagcgga aagatggccg cttcccggcc ctgctgcagg    3960
gagctcaaaa tggaggacgc ggcgctcggg agagcgggcg ggtgagtcac ccacacaaag    4020
gaaaagggcc tttccgtcct cagccgtcgc ttcatgtgac tccacggagt accgggcgcc    4080
gtccaggcac ctcgattagt tctcgagctt ttggagtacg tcgtctttag gttgggggga    4140
ggggttttat gcgatggagt ttccccacac tgagtgggtg gagactgaag ttaggccagc    4200
ttggcacttg atgtaattct ccttggaatt tgccctttt gagtttggat cttggttcat     4260
tctcaagcct cagacagtgg ttcaaagttt ttttcttcca tttcaggtgt cgtgagaatt    4320
caccatggag ctgaggccct ggttgctatg ggtggtagca gcaacaggaa ccttggtcct    4380
gctagcagct gatgctcagg gccagaaggt cttcaccaac acgtgggctg tgcgcatccc    4440
tggaggccca gcgtggccca acagtgtggc acgaagcat gggttcctca acctgggcca     4500
gatcttcggg gactattacc acttctggca tcgaggagtg acgaagcggt ccctgtcgcc    4560
tcaccgcccg cggcacagcc ggctgcagag ggagcctcaa gtacagtggc tggaacagca    4620
ggtggcaaag cgacggacta acgggacgt gtaccaggag cccacagacc caagttttcc     4680
tcagcagtgg tacctgtctg gtgtcactca gcgggacctg aatgtgaagg cggcctgggc    4740
gcagggctac acagggcacg gcattgtggt ctccattctg gacgatggca tcgagaagaa    4800
ccaccccgac ttggcaggca attatgatcc tgggccagt tttgatgtca atgaccagga     4860
ccctgacccc cagcctcggt acacacagat gaatgacaac aggcacggca cggtgtgc     4920 ggggaagtg gctgcggtgg ccaacaacg tgtctgtggt gtaggtgtgg cctacaacgc      4980
ccgcattgga ggggtgcgca tgctggatgg cgaggtgaca gatgcagtgg aggcacgctc    5040
gctgggcctg aaccccaacc acatccacat ctacagtgcc agctgggccc cgaggatga    5100 cggcaagaca gtggatgggc cagcccgcct cgccgaggag gccttcttcc gtgggtttag    5160
ccagggccga gggggggctgg gctccatctt tgtctgggcc tcggggaacg ggggccggga   5220
acatgacagc tgcaactgcg acggctacac caacagtatc tacacgctgt ccatcagcag    5280
cgccacgcag tttggcaacg tgccgtggta cagcgaggcc tgctcgtcca cactggccac    5340
gacctacagc agtggcaacc agaatgagaa gcagatcgtg acgactgact tgcggcagaa    5400
gtgcacggag tctcacacgg gcacctcagc ctctgccccc ttagcagccg gcatcattgc    5460
tctcaccctg gaggccaata gaaacctcac atggcgggac atgcaacacc tggtggtaca    5520
gacctcgaag ccagcccacc tcaatgccaa cgactgggcc accaatggtg tgggccggaa    5580
agtgagccac tcatatggct acgggcttt ggacgcaggc gccatggtgg ccctggccca     5640
gaattggacc acagtggccc cccagcggaa gtgcatcatc gacatcctca ccgagcccaa    5700
agacatcggg aaacggctcg aggtgcggaa gaccgtgacc gcgtgcctgg gcagcccaa     5760 ccacatcact cggctggagc acgctcaggc gcggctcacc ctgtcctata atcgccgtgg    5820
cgacctggcc atccacctgg tcagccccat gggcacccgc tccacccctgc tggcagccag   5880
```

```
gccacatgac tactccgcag atgggtttaa tgactgggcc ttcatgacaa ctcattcctg    5940
ggatgaggat ccctctggcg agtgggtcct agagattgaa acaccagcg aagccaacaa     6000 ctatgggacg ctgaccaagt tcaccctcgt actctatggc accgcccctg aggggctgcc    6060
cgtacctcca gaaagcagtg gctgcaagac cctcacgtcc agtcaggcct gtgtggtgtg    6120
cgaggaaggc ttctccctgc accagaagag ctgtgtccag cactgccctc caggcttcgc    6180
cccccaagtc ctcgatacgc actatagcac cgagaatgac gtggagacca tccgggccag    6240
cgtctgcgcc ccctgccacg cctcatgtgc cacatgccag gggccggccc tgacagactg    6300
cctcagctgc cccagccacg cctccttgga ccctgtggag cagacttgct cccggcaaag    6360
ccagagcagc cgagagtccc cgccacagca gcagccacct cggctgcccc cggaggtgga    6420
ggcggggcaa cggctgcggg cagggctgct gccctcacac ctgcctgagg tggtggccgg    6480
cctcagctgc gccttcatcg tgctggtctt cgtcactgtc ttcctggtcc tgcagctgcg    6540
ctctggcttt agttttcggg gggtgaaggt gtacaccatg accgtgcc tcatctccta      6600 caaggggctg cccctgaag cctggcagga ggagtgcccg tctgactcag aagaggacga     6660
gggccggggc gagaggaccg cctttatcaa agaccagagc gccctctgat gagcccactg    6720 cccacccct caagccaatc ccctccttgg gcacttttta attcaccaaa gtatttttt      6780 atctgtcggg ttcgaaatcg atgcggccgc tcgagtctag agggcccgtt taaacccgct    6840
gatcagcctc gactgtgcct tctagttgcc agccatctgt tgtttgcccc tccccgtgc     6900 cttccttgac cctggaaggt gccactccca ctgtcctttc ctaataaaat gaggaaattg    6960
catcgcattg tctgagtagg tgtcattcta ttctgggggg tggggtgggg caggacagca    7020 aggggagga ttgggaagac aatagcaggc atgctggga tgcggtgggc tctatggctt      7080
ctgaggcgga aagaaccagc tggggctcta ggggtatcc ccacgcgccc tgtagcggcg     7140
cattaagcgc ggcgggtgtg gtggttacgc gcagcgtgac cgctacactt gccagcgccc    7200
tagcgcccgc tcctttcgct ttcttccctt cctttctcgc cacgttcgcc ggctttcccc    7260
gtcaagctct aaatcggggg tccctttagg gttccgattt agtgctttac ggcacctcga    7320
ccccaaaaaa cttgattagg gtgatggttc acgtacctag aagttcctat tccgaagttc    7380
ctattctcta gaaagtatag gaacttcctt ggccaaaaag cctgaactca ccgcgacgtc    7440
tgtcgagaag tttctgatcg aaaagttcga cagcgtctcc gacctgatgc agctctcgga    7500
gggcgaagaa tctcgtgctt tcagcttcga tgtaggaggg cgtggatatg tcctgcgggt    7560
aaatagctgc gccgatggtt tctacaaaga tcgttatgtt tatcggcact ttgcatcggc    7620
cgcgctcccg attccggaag tgcttgacat tggggaattc agcgagagcc tgacctattg    7680
catctcccgc cgtgcacagg gtgtcacgtt gcaagacctg cctgaaaccg aactgcccgc    7740
tgttctgcag ccggtcgcgg aggccatgga tgcgatcgct gcggccgatc ttagccagac    7800
gagcgggttc ggcccattcg gaccgcaagg aatcggtcaa tacactacat ggcgtgattt    7860
catatgcgcg attgctgatc cccatgtgta tcactggcaa actgtgatgg acgacaccgt    7920
cagtgcgtcc gtcgcgcagg ctctcgatga gctgatgctt tgggccgagg actgccccga    7980
agtccggcac ctcgtgcacg cggatttcgg ctccaacaat gtcctgacgg acaatggccg    8040
cataacagcg gtcattgact ggagcgaggc gatgttcggg gattcccaat acgaggtcgc    8100
caacatcttc ttctggaggc cgtggttggc ttgtatggag cagcagacgc gctacttcga    8160
gcggaggcat ccggagcttg caggatcgcc gcggctccgg gcgtatatgc tccgcattgg    8220
```

```
tcttgaccaa ctctatcaga gcttggttga cggcaatttc gatgatgcag cttgggcgca   8280
gggtcgatgc gacgcaatcg tccgatccgg agccgggact gtcgggcgta cacaaatcgc   8340
ccgcagaagc gcggccgtct ggaccgatgg ctgtgtagaa gtactcgccg atagtggaaa   8400
ccgacgcccc agcactcgtc cgagggcaaa ggaatagcac gtactacgag atttcgattc   8460
caccgccgcc ttctatgaaa ggttgggctt cggaatcgtt ttccgggacg ccggctggat   8520
gatcctccag cgcggggatc tcatgctgga gttcttcgcc cacccccaact tgtttattgc   8580
agcttataat ggttacaaat aaagcaatag catcacaaat ttcacaaata aagcattttt   8640
ttcactgcat tctagttgtg gtttgtccaa actcatcaat gtatcttatc atgtctgtat   8700
accgtcgacc tctagctaga gcttggcgta atcatggtca tagctgtttc ctgtgtgaaa   8760
ttgttatccg ctcacaattc cacacaacat acgagccgga agcataaagt gtaaagcctg   8820
gggtgcctaa tgagtgagct aactcacatt aattgcgttg cgctcactgc ccgctttcca   8880
gtcgggaaac ctgtcgtgcc agctgcatta atgaatcggc caacgcgcgg ggagaggcgg   8940
tttgcgtatt gggcgctctt ccgcttcctc gctcactgac tcgctgcgct cggtcgttcg   9000
gctgcggcga gcggtatcag ctcactcaaa ggcggtaata cggttatcca cagaatcagg   9060
ggataacgca ggaaagaaca tgtgagcaaa aggccagcaa aaggccagga accgtaaaaa   9120
ggccgcgttg ctggcgtttt tccataggct ccgcccccct gacgagcatc acaaaaatcg   9180
acgctcaagt cagaggtggc gaaacccgac aggactataa agataccagg cgtttccccc   9240
tggaagctcc ctcgtgcgct ctcctgttcc gaccctgccg cttaccggat acctgtccgc   9300
ctttctccct tcgggaagcg tggcgctttc tcatagctca cgctgtaggt atctcagttc   9360
ggtgtaggtc gttcgctcca agctgggctg tgtgcacgaa ccccccgttc agcccgaccg   9420
ctgcgcctta tccggtaact atcgtcttga gtccaacccg gtaagacacg acttatcgcc   9480
actggcagca gccactggta acaggattag cagagcgagg tatgtaggcg gtgctacaga   9540
gttcttgaag tggtggccta actacggcta cactagaagg acagtatttg gtatctgcgc   9600
tctgctgaag ccagttacct tcggaaaaag agttggtagc tcttgatccg gcaaacaaac   9660
caccgctggt agcggtggtt tttttgtttg caagcagcag attacgcgca gaaaaaaagg   9720
atctcaagaa gatcctttga tcttttctac ggggtctgac gctcagtgga acgaaaactc   9780
acgttaaggg attttggtca tgagattatc aaaaaggatc ttcacctaga tccttttaaa   9840
ttaaaaatga agttttaaat caatctaaag tatatatgag taaacttggt ctgacagtta   9900
ccaatgctta atcagtgagg cacctatctc agcgatctgt ctatttcgtt catccatagt   9960
tgcctgactc cccgtcgtgt agataactac gatacgggag ggcttaccat ctggccccag  10020
tgctgcaatg ataccgcgag acccacgctc accggctcca gatttatcag caataaacca  10080
gccagccgga agggccgagc gcagaagtgg tcctgcaact ttatccgcct ccatccagtc  10140
tattaattgt tgccgggaag ctagagtaag tagttcgcca gttaatagtt tgcgcaacgt  10200
tgttgccatt gctacaggca tcgtggtgtc acgctcgtcg tttggtatgg cttcattcag  10260
ctccggttcc caacgatcaa ggcgagttac atgatccccc atgttgtgca aaaaagcggt  10320
tagctccttc ggtcctccga tcgttgtcag aagtaagttg gccgcagtgt tatcactcat  10380
ggttatggca gcactgcata attctcttac tgtcatgcca tccgtaagat gcttttctgt  10440
gactggtgag tactcaacca agtcattctg agaatagtgt atgcggcgac cgagttgctc  10500
ttgcccggcg tcaatacggg ataataccgc gccacatagc agaactttaa aagtgctcat  10560
cattggaaaa cgttcttcgg ggcgaaaact ctcaaggatc ttaccgctgt tgagatccag  10620
```

```
ttcgatgtaa cccactcgtg cacccaactg atcttcagca tcttttactt tcaccagcgt    10680
ttctgggtga gcaaaaacag gaaggcaaaa tgccgcaaaa aagggaataa gggcgacacg    10740
gaaatgttga atactcatac tcttcctttt tcaatattat tgaagcattt atcagggtta    10800
ttgtctcatg agcggataca tatttgaatg tatttagaaa aataaacaaa tagggggttcc    10860 gcgcacattt ccccgaaaag tgccacctga cgtc                                10894

<210> SEQ ID NO 8
<211> LENGTH: 17
<212> TYPE: PRT
<213> ORGANISM: Artificial Sequence
<220> FEATURE:
<223> OTHER INFORMATION: Synthetic

<400> SEQUENCE: 8

Gly Ser Ala Pro Thr Lys Ala Lys Arg Arg Val Val Gln Arg Glu Lys
1               5                   10                  15
Arg

<210> SEQ ID NO 9
<211> LENGTH: 4
<212> TYPE: PRT
<213> ORGANISM: Artificial Sequence
<220> FEATURE:
<223> OTHER INFORMATION: Synthetic

<400> SEQUENCE: 9

Arg Glu Lys Arg
1

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Arg Arg Arg Arg Arg Arg
1               5
```

MATERIALS AND METHODS FOR PRODUCING CLEAVED, HIV-1 ENVELOPE GLYCOPROTEIN TRIMERS

CROSS-REFERENCE TO RELATED APPLICATIONS

This patent application is the U.S. national phase of International Patent Application PCT/US2015/19486, filed on Mar. 9, 2015, which claims the benefit of U.S. Provisional Patent Application No. 61/949,742, filed Mar. 7, 2014, which are incorporated by reference in there entireties herein.

STATEMENT REGARDING FEDERALLY SPONSORED RESEARCH AND DEVELOPMENT

This invention was made with government support under AI082362 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 41,126 Byte ASCII (Text) file named "726448_ST25-Revised.TXT" created on Sep. 28, 2017.

BACKGROUND OF THE INVENTION

The development of a vaccine against HIV-1 infection remains a significant global health problem. One of the major vaccine design concepts is the induction of high titer broadly neutralizing antibodies (bNAbs) that are capable of preventing HIV-1 entry into target cells, and hence intervening against virus transmission (Burton et al., *Nat. Immunol.,* 5: 233-236 (2004)). A relevant target for bNAbs is the envelope, or Env, glycoprotein complex, or spike, on the virus surface (Zwick et al., *Curr. HIV. Res.,* 5: 608-624 (2007); Walker et al., *Curr. Opin. Immunol.,* 22: 358-366 (2010)). This complex, a trimer of gp120/gp41 heterodimers, attaches to receptors on target cells and then mediates fusion of the viral and cell membranes (Liu et al., *Nature,* 455: 109-113 (2008)). Any antibodies that can bind to a sufficient number of functional Env spikes will impede one or more stages in the receptor-binding and fusion process, thereby neutralizing infectivity (Zwick et al., *Curr. HIV. Res.,* 5: 608-624 (2007)).

The development of vaccines which induce bNAbs remains elusive. One potential strategy is to create structural and antigenic mimics of the native, virion-associated Env spike. To do so a stop codon is inserted to truncate the gp41 protein prior to the membrane-spanning domain, thereby yielding soluble proteins that can be secreted from producer cells and purified. Unfortunately, without suitable sequence modifications, soluble gp140s are highly unstable and either disintegrate completely into their constituents or adopt non-native configurations that may be compromised from the perspective of bNAb induction (Guttman et al., *J. Virol.,* 87: 11462-11475 (2013); Ringe et al., *Proc. Natl. Acad. Sci. U.S.A.,* 110: 18256-18261 (2013)). One effective strategy for making soluble, native-like trimers involves introducing "SOSIP" modifications: (i) a disulfide bond (designated SOS) to link the gp120 and gp41 ectodomain ($gp41_{ECTO}$) components, and (ii) a point substitution (I559P) in $gp41_{ECTO}$ that creates additional stability (Sanders et al., *J. Virol.,* 76: 8875-8889 (2002); Binley et al., *J. Virol.,* 74: 627-643 (2000); Binley et al., *J. Virol.,* 76: 2606-2616 (2002)). Proteolytic cleavage between the gp120 and gp41 subunits is also critical for making native-like trimers, and is facilitated by optimizing the cleavage site and co-expressing the furin protease (Binley et al., *J. Virol.,* 74: 627-643 (2000); Binley et al., *J. Virol.,* 76: 2606-2616 (2002)). At present, the most advanced soluble, cleaved trimers, based on a subtype A founder virus, are designated BG505 SOSIP.664 (Sanders et al., *PLoS Pathog.,* 9: e1003618 (2013); Wu et al., *J. Virol.,* 80: 835-844 (2006); Hoffenberg et al., *J. Virol.,* 87: 5372-5383 (2013)). These highly homogeneous trimers closely resemble virus spikes when visualized by negative stain electron microscopy (EM) (Sanders et al., *PLoS Pathog.,* 9: e1003618 (2013)). They also have highly favorable antigenic properties, expressing multiple bNAb epitopes while occluding most epitopes for non-neutralizing antibodies (non-NAbs) (Ringe et al., *Proc. Natl. Acad. Sci. U.S.A.,* 110: 18256-18261 (2013); Sanders et al., *PLoSPathog.,* 9: e1003618 (2013)). In addition, the structure of these trimers has been determined by both x-ray diffraction and cryo-EM at ~5-6 Å resolution (Julien et al., *Science,* 342: 1477-1483 (2013); Lyumkis et al., *Science,* 342: 1484-1490 (2013)).

A need remains for methods facilitating the production and manufacture of HIV Env glycoproteins (such as BG505 SOSIP.664 gp140 trimers), of sufficient quality, and in sufficient quantity, to serve as pre-clinical research reagents, and clinical-grade immunogens.

BRIEF SUMMARY OF THE INVENTION

In one aspect, the invention provides an expression vector. The vector comprises a first nucleic acid sequence encoding an HIV Env glycoprotein and a second nucleic acid sequence encoding a furin protease, wherein (i) expression of the nucleic acid sequence encoding the Env glycoprotein is controlled by a first constitutive promoter and the expression of the nucleic acid sequence encoding the furin protease is controlled by a second constitutive promoter, (ii) the first constitutive promoter is more potent than the second constitutive promoter, and (iii) the expression vector integrates into the genome of a mammalian cell.

The invention further provides a mammalian cell comprising the aforementioned expression vector. The mammalian cell expresses furin-cleaved HIV Env glycoproteins.

The invention also provides a method of generating a mammalian cell line that expresses cleaved HIV Env glycoproteins. The method comprises (a) transfecting one or more mammalian cells with the aforementioned expression vector of the invention under conditions wherein the expression vector integrates into the genome of the one or more mammalian cells, (b) selecting one or more mammalian cells comprising the expression vector integrated into the genome thereof and expressing cleaved HIV Env glycoproteins, and (c) propagating the selected mammalian cells indefinitely, thereby generating a mammalian cell line that expresses cleaved HIV Env glycoproteins.

The invention also provides a method of producing cleaved Env glycoproteins. The method comprises (i) culturing an isolated mammalian cell comprising the aforementioned expression vector under conditions to express the first and second nucleic acid sequences to provide HIV Env glycoproteins and furin proteases, and (ii) allowing the furin protease to cleave the Env glycoproteins to provide cleaved Env glycoproteins.

BRIEF DESCRIPTION OF THE DRAWINGS

FIG. 5 is a blot depicting the results of a BN-PAGE analysis of 2G12-purified Env glycoproteins produced by the BG505 SOSIP.664-expressing 293T and CHO stable cell lines. The gels were stained with Coomassie blue. The molecular weights of marker (M) proteins (thyroglobulin, 669 kDa and ferritin, 440 kDa) are indicated.

DETAILED DESCRIPTION OF THE INVENTION

Figure 1:
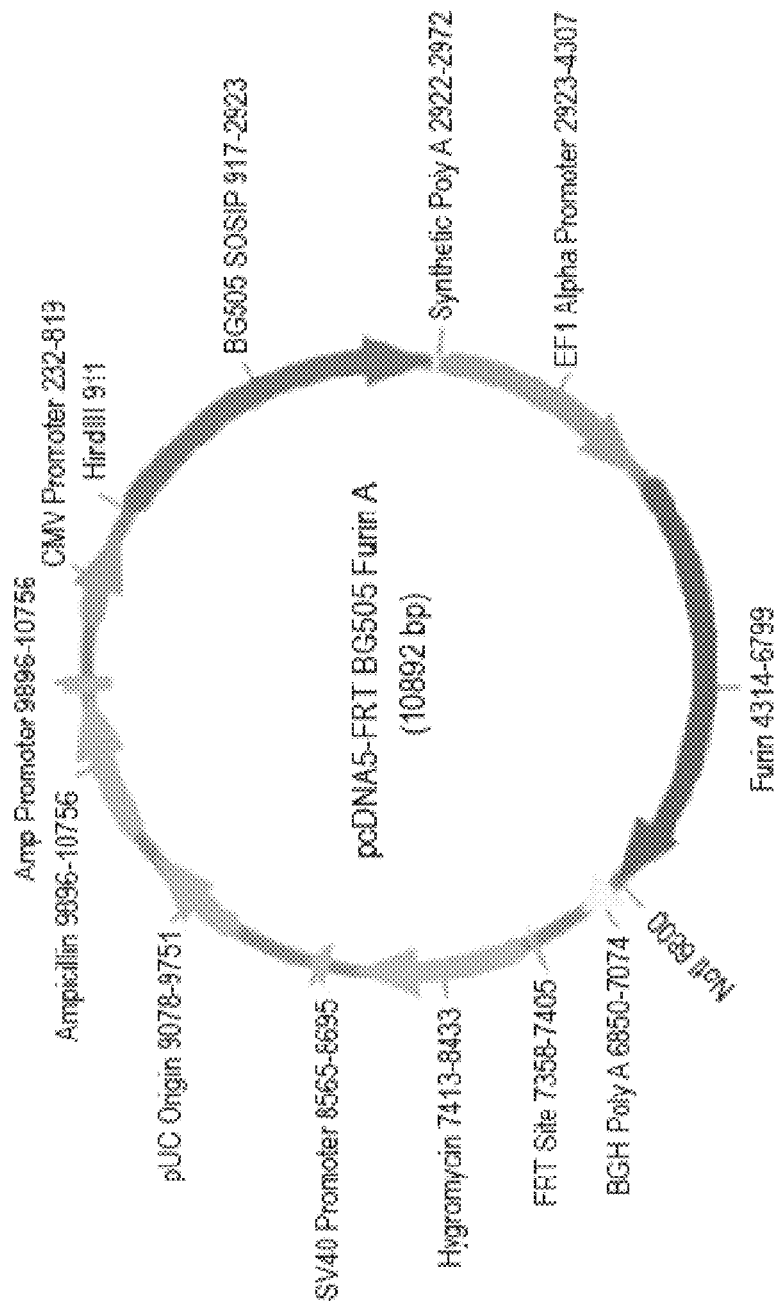
FIG. 1 is a diagram depicting the design of the pAM/C construct for expressing BG505 SOSIP.664 gp140. The plasmid map shows the site of the Env glycoprotein and furin gene insertions, the promoters, and the Poly A sequence.

The invention provides an expression vector comprising nucleic acid sequences encoding an HIV Env glycoprotein and furin. As used herein, "expression vector" refers to a plasmid or virus designed to express a protein of interest in cells. In one embodiment the expression vector is a plasmid. "Plasmid" refers to small DNA molecules physically separated from chromosomal DNA. The plasmid may be, e.g., a circular, double stranded DNA molecule.

Any suitable expression vector or vector system, e.g., a recombinant vector, can be used in accordance with the invention, so long as the expression vector or vector system can be transfected into mammalian cells and can comprise nucleic acid sequences encoding an HIV Env glycoprotein and furin as described herein. Preferably, the expression vector integrates into the genome of the mammalian cells. Examples of vectors that integrate in a site specific manner include, for example, components of the Flp-In™ system (Invitrogen, Carlsbad, Calif.) (e.g., pcDNA™5/FRT), or the cre-lox system, such as can be found in the pExchange-6 core vectors (Stratagene, La Jolla, Calif.). In a preferred embodiment, the expression vector is a pcDNA™5/FRT vector suitable for use with the Flp-In™ expression system (Invitrogen, Carlsbad, Calif.).

Viral expression vectors also can be used. Representative viral expression vectors include, for example, the adenovirus-based vectors (e.g., the adenovirus-based Per.C6 system available from Crucell, Inc. (Leiden, The Netherlands)), lentivirus-based vectors (e.g., the lentiviral-based pLPI from Life Technologies (Carlsbad, Calif.)), and retroviral vectors (e.g., the pFB-ERV plus pCFB-EGSH from Stratagene (La Jolla, Calif.)).

As used herein, "HIV Env glycoprotein" or "Env glycoprotein" refers to the Env complexes, or spikes, which occur on the HIV virion surface (see e.g. Zwick et al., *Curr. HIV. Res.*, 5: 608-624 (2007); Walker et al., *Curr. Opin. Immunol.*, 22: 358-366 (2010)). This complex occurs in nature as a trimer of gp120/gp41 heterodimers. A gene encoding an HIV Env glycoprotein is referred to herein as an "env" gene. The HIV Env glycoprotein, and the nucleic acid sequence encoding it, may be derived from any strain, group, or clade (subtype) of the HIV virus. In one embodiment the HIV Env glycoprotein is derived from HIV-1, group M. In especially preferred embodiments the HIV Env glycoprotein is derived from Subtypes A, B or C. Preferably, the HIV Env glycoprotein is derived from virus BG505 (a Subtype A virus). In another preferred embodiment the HIV Env glycoprotein is derived from B41, an env gene isolated from a Subtype B founder virus. In another preferred embodiment, the HIV Env glycoprotein is derived from a Subtype C virus. The HIV Env glycoprotein may also be a genetically modified Env protein and/or Env protein fragment. Suitable Env proteins are known in the art and include, for example, gp160, gp120, gp41, gp145, and gp140. In a preferred embodiment the HIV Env glycoprotein is gp140 or a modified gp140. In preferred embodiments, the HIV Env glycoproteins form trimers. The Env glycoproteins may also be fusion proteins. For example, all or part of an HIV Env protein (e.g., gp120 or gp160), can be fused to all or part of another HIV protein such as Pol.

The expression vector of the invention comprises a nucleic acid sequence encoding an HIV Env glycoprotein. To optimize protein production, the nucleic acid sequence encoding the HIV Env glycoprotein can further comprise a polyadenylation site following the coding region of the nucleic acid molecule. Any suitable polyadenylation sequence can be used, including a synthetic optimized sequence, as well as the polyadenylation sequence of BGH (Bovine Growth Hormone), polyoma virus, TK (Thymidine Kinase), EBV (Epstein Barr Virus), and the papillomaviruses, including human papillomaviruses and BPV (Bovine Papilloma Virus) and SV40 (Human Sarcoma Virus-40). In one embodiment, the polyadenylation sequence is a synthetic Poly A modeled from the HSV Thymidine Kinase Poly A (New England BioLabs, Ipswich, Mass.). Also, preferably all the proper transcription signals (and translation signals, where appropriate) will be correctly arranged such that the exogenous nucleic acid will be properly expressed in the cells into which it is introduced. Moreover, the nucleic acid sequence can further comprise the appropriate sequences for processing, secretion, intracellular localization, and the like.

In a one embodiment, the first nucleic acid sequence encoding an HIV Env glycoprotein is genetically modified such that the gp41 domain of the HIV Env glycoprotein is truncated prior to the hydrophobic membrane spanning domain resulting in a $gp41_{ECTO}$ domain. This can be achieved, for example, by introducing a stop codon at $gp41_{ECTO}$ residue 664 to improve homogeneity and solubility (see Khayat et al., *J. Virol.*, 87: 9865-9872 (2013); Klasse et al., *J. Virol.*, 87: 9873-9885 (2013)). The resultant HIV Env glycoproteins are trimers of $gp120/gp41_{ECTO}$ heterodimers.

In an another embodiment, the first nucleic acid sequence encoding an HIV glycoprotein is genetically modified such that a disulfide bond (designated SOS) is introduced into the HIV Env glycoprotein linking the gp120 domain and the $gp41_{ECTO}$ domains. This can be achieved by, for example, substituting residues A501 and T605 in the Env glycoprotein with cysteine. Preferably the isoleucine occurring at position 559 of the $gp41_{ECTO}$ domain is substituted with proline. These modifications are referred to collectively as "SOSIP modifications."

In addition to the aforementioned modifications, the Env glycoprotein can comprise other modifications, such as, for example, the substitution of REKR (SEQ ID NO: 9) to RRRRRR (SEQ ID NO: 10) in gp120 for cleavage enhancement, (see Binley et al., *J. Virol.*, 76: 2606-2616 (2002)), and the insertion of a TPA leader peptide to increase gene expression (see Sanders et al., *PLoS Pathog.*, 9: e1003618 (2013); Sellhorn et al., *Vaccine*, 28: 430-436 (2009)). These and other modifications can be introduced via methods known in the art such as, e.g., site-directed mutagenesis. It will further be understood that HIV Env glycoproteins expressed in mammalian cells may undergo post-translational modification. Post translational modifications associated with mammalian expression may include, without limitation, phosphorylation, glycosylation, carboxylation, ubiquitination, myristylation, or lipidation.

In a preferred embodiment, the HIV Env glycoprotein is BG505 SOSIP.664 (the amino acid sequence of which comprises SEQ ID NO: 1). BG505 SOSIP.664 is an HIV Env glycoprotein expressed derived from HIV subtype A transmitted/founder strain BG505 in which the SOS and I559P modifications have been introduced (see, e.g., Sanders et al., *PLoS Pathog.*, 9: e1003618 (2013); Wu et al., *J. Virol.*, 80: 835-844 (2006); Hoffenberg et al., *J. Virol.*, 87: 5372-5383 (2013)). The nucleotide sequence encoding BG505 SOSIP.664 is provided as SEQ ID NO: 2. In another preferred embodiment, the HIV Env glycoprotein is B41 SOSIP.664 (the amino acid sequence of which comprises SEQ ID NO: 3). The nucleotide sequence encoding B41 SOSIP.664 is provided as SEQ ID NO: 4. The B41 SOSIP.664 protein is based on a Subtype B HIV virus. It is modified relative to wild type in similar fashion to BG505 SOSIP.664 (see Pugach et al., *J. Virol.*, Advance online publication, doi: 10112/JVI.03473-14 (2015)). In another preferred embodiment, the HIV Env Glycoprotein is a SOSIP modified HIV Env glycoprotein derived from an HIV clade C virus (the amino acid sequence of which comprises SEQ ID NO: 5). The nucleotide sequence encoding the Env glycoprotein derived from an HIV clade C virus is provided as SEQ ID NO: 6. It will be understood that the vectors described herein can be readily adapted to facilitate the insertion of other HIV Env glycoprotein genes.

The expression vector of the invention also comprises a second nucleic acid sequence encoding furin protease. Furin protease is a calcium-dependent serine endoprotease that cleaves various precursor proteins. It is known in the art as one of the proteases responsible for the proteolytic cleavage of the HIV env proteins gp160 and gp140 (Hallenberger et al., *Nature*, 360(6402): 358-61 (1992)). To optimize furin protease production, the nucleic acid sequence encoding the furin protease preferably includes all the proper transcription signals (and translation signals, where appropriate). Moreover, the nucleic acid sequence can further comprise the appropriate sequences for processing, secretion, intracellular localization, and the like.

In one aspect, the expression vector of the present invention is capable of co-expressing an Env glycoprotein and furin protease, such that the furin protease is expressed in mammalian cells at levels sufficient to affect efficient HIV Env glycoprotein cleavage without inducing toxicity to the host cells. Accordingly, the first nucleic acid sequence encoding the HIV Env glycoprotein is operably linked to a first promoter, while the second nucleic acid sequence encoding furin protease is operably linked to a second, different, promoter. Each of the first and second promoters can be any suitable promoter obtained or derived from any source, and desirably is a constitutive promoter or an inducible promoter. A constitutive promoter is a promoter that actively promotes transcription of the regulated gene at all times in the cell. An inducible promoter becomes active only in response to specific stimuli. In one embodiment, each of the first promoter and second promoter is a constitutive promoter.

A large number of promoters, including constitutive, and inducible, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, and the Rous Sarcoma Virus promoter. Inducible promoters include, for example, the Tet system (U.S. Pat. Nos. 5,464,758 and 5,814,618), the Ecdysone inducible system (No et al., *Proc. Natl. Acad. Sci.*, 93: 3346-3351 (1996)), the T-REx™ system (Invitrogen, Carlsbad, Calif.), LACSWITCH™ system (Stratagene, San Diego, Calif.), and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)).

In one embodiment, either or both the first promoter or the second promoter can be a viral promoter. Suitable viral promoters include, for instance, cytomegalovirus (CMV) promoters, such as the CMV immediate-early promoter (described in, for example, U.S. Pat. Nos. 5,168,062 and 5,385,839), promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the Lap2 promoter or the herpes thymidine kinase promoter (Wagner et al., *Proc. Natl. Acad. Sci.*, 78, 144-145 (1981)), promoters derived from SV40 or Epstein Barr virus, an adeno-associated viral promoter, such as the p5 promoter, and the like. A preferred viral promoter for use in the invention is a CMV promoter.

In another embodiment, either or both the first promoter and the second promoter can be a eukaryotic cellular promoter, i.e., a promoter that drives expression of a cellular protein. Preferred eukaryotic cellular promoters for use in the invention will depend on the desired expression profile to produce the HIV Env glycoprotein and/or furin protease. In one aspect, the cellular promoter is preferably a constitutive promoter that works in a variety of cell types. Suitable constitutive promoters can drive expression of genes encoding transcription factors, housekeeping genes, or structural genes common to eukaryotic cells. A preferred eukaryotic cellular promoter for use in the invention is the constitutive promoter human elongation factor-1 alpha or EF1-alpha.

In one embodiment, the activity of the first promoter is greater than the activity of the second promoter, that is, the first promoter is more potent than the second promoter. Ideally, the activity of the first promoter is at least 2-fold greater than, but not more than 20-fold greater than, the activity of the second promoter. For example, the activity of the first promoter can be about 3-fold, about 5-fold, about 10-fold, about 12-fold, or about 15-fold greater than the activity of the second promoter. It will be understood that the activity of a given promoter, and therefore the relative activity of the first and second promoters, may vary from cell-type to cell-type. The activity of the first and second promoters can be determined by using standard assays for measuring gene expression, which include but are not limited to northern blotting, RT-qPCR, serial analysis of gene expression (SAGE), and/or whole transcriptome shotgun sequencing (WTSS or RNA-Seq).

In a preferred embodiment, the first promoter is CMV and the second promoter is EF1-alpha.

In accordance with the invention, the expression vector is transfected into a mammalian cell. The mammalian cell can be any mammalian cell suitable for expression. The mammalian cell can be, for example, selected from the group consisting of CHO cells, 293T cells, COS cells, HEK293 cells, 3T3 cells, NS0 cells, Sp20 cells, Vero cells, HeLa cells HepG2 cells, SkHep cells, and BHK cells. In some preferred embodiments, the mammalian cell is a CHO cell. In other preferred embodiments the mammalian cell is a 293T cell. The mammalian cell can comprise any modification deemed useful, for example, in protein expression generally, or expression of the HIV Env glycoprotein specifically. For example, suitable CHO cells can be dihydrofolate reductase (DHFR)-deficient, or modified to include a tetracycline repressor or an expression control vector, or have some other recombinant or selected modification. Cells suitable for use in the invention are capable of producing proteins having at least one post-translational modification typically understood by one of ordinary skill in the art to be associated with mammalian expression.

The invention provides for a mammalian cell transformed or transfected with an expression vector. Means of transforming, or transfecting, cells with exogenous DNA molecules are well known in the art. For example, without limitation, a DNA molecule is introduced into a cell using standard transformation or transfection techniques well known in the art such as calcium-phosphate or DEAE-dextran-mediated transfection, protoplast fusion, electroporation, liposomes and direct microinjection (see, e.g., Sambrook & Russell, Molecular Cloning: A Laboratory Manual, Cold Spring Harbor Laboratory Press, New York (2001), pp. 1.1-1.162, 15.1-15.53, 16.1-16.54). A widely used method for transformation is transfection mediated by either calcium phosphate or DEAE-dextran.

According to the invention the expression vector is integrated within the genome of the host mammalian cell. This integration can be achieved via methods known in art. In a preferred embodiment, the mammalian cells and expression vector are components of the Flp-In™ System (Invitrogen, Carlsbad, Calif.). The mammalian cells are co-transfected with a pOG44 Flp recombinase plasmid and the expression vector. The expression vector is then integrated into the host cell genome in an Flp-recombinase-dependent manner. Briefly, integration occurs via recombination between specific FRT sites on the interacting DNA molecules, e.g. the expression vector and host genome (pcDNA™5/FRT Vector, Instruction Manual, Ver. pp. 1-8. Invitrogen, USA 2012). The FRT site, originally isolated from *Saccharomyces cerevisiae*, serves as a binding site for Flp recombinase and has been well-characterized (see Gronostajski et al, *J. Biol. Chem.*, 260, 12320-12327 (1985); Jayaram, *Proc. Natl. Acad. Sci. USA*, 82: 5875-79 (1985); Sauer, *Curr. Opin. Biotechnol.* 5: 521-27 (1994); Senecoff et al., *Proc. Natl. Acad. Sci. USA*, 82: 7270-74 (1985)). Cell lines suitable for use in the Flp-In™ System contain a single integrated FRT site. Exemplary cell lines include Flp-In™-CHO cells and Flp-In™-293 cells (Invitrogen, Carlsbad, Calif.).

The isolation of stably transformed cells requires the introduction of a selectable marker in conjunction with the transformation with expression vector. For example, the expression vector may contain a gene for hygromycin resistance providing for the selection of transformed cells with the antibiotic hygromycin B. In one embodiment, it is possible to select for cells in which the expression vector has been successfully integrated into the host genome. For example in the Flp-In™ System, the hygromycin gene in the pcDNA™5/FRT Vector lacks a promoter and is active only after it is integrated in the host genome (see pcDNA™5/FRT Vector, Instruction Manual, Invitrogen, USA (2012)).

The invention also provides a method of producing cleaved HIV Env glycoproteins, by culturing the cell lines co-expressing HIV Env glycoprotein and furin protease. Methods for culturing appropriate mammalian cell-lines are known in the art (see, e.g., Growth and Maintenance of Flp-In™ Cell Lines, Instruction Manual, Rev. 3, Invitrogen (2013)). Generally, cells are grown and maintained at an appropriate temperature and gas mixture in a cell incubator. For example, for mammalian cells, typical conditions include a temperature of approximately 37° C., and a $CO_2$ concentration of approximately 5%. The cells may be grown either in suspended or adherent cell cultures. Any appropriate cell growth medium may be used. It will be understood that the growth medium may vary in pH, glucose concentration, and nutrient concentration. The growth medium may include one or more growth factors, including, for example, fetal bovine serum (FBS), bovine calf serum, equine serum and/or porcine serum. In some embodiments the growth medium contains 10%, 5%, or 1% FBS. In other embodiments, the growth medium is serum free.

The methods of the invention can be adapted for the manufacture of GMP-compliant lines that could serve as, for example, the sources of BG505 SOSIP.664 gp140 trimers for human testing as vaccine antigens. CHO cell lines, for example, are commonly employed to make clinical grade recombinant proteins.

The invention provides for the development of mammalian cell lines, which produce high quality, cleaved HIV Env glycoprotein trimers that are capable of generating bNAbs at yields of up to 12-15 mg per $1\times10^9$ cells. Preferably, expression at such levels is maintained for up to 30 days after initial seeding and is consistently superior to what could be achieved by transient transfection. Preferably, the HIV Env glycoproteins generated by the cell lines have the same native-like appearance as those derived by transient transfection as confirmed by, for example, electron microscopy analysis. The Env glycoproteins also desirably have appropriate antigenic properties, including, preferably, the presentation of the quaternary epitope for the broadly neutralizing antibody PGT145. Preferably, the mammalian cell lines can be propagated indefinitely.

In a particular embodiment of the invention, the Flp-In™ system from Invitrogen (Carlsbad, Calif.) is used to make 293T and CHO cell lines that yield substantial amounts (e.g., up to 12-15 mg from $1\times10^9$ cells) of high quality BG505 SOSIP.664 gp140 trimers. The purified trimers are fully cleaved, have appropriate antigenic properties, and, when viewed by negative stain electron microscopy (EM), appear identical to ones produced by transient transfection (see Ringe et al., supra; Sanders et al. (2013), supra). The method used to make the cell lines is adaptable to Good Manufacturing Practice (GMP) conditions appropriate for producing immunogens for human vaccine trials.

While the expression vectors and methods discussed herein are directed towards the creation of cell lines expressing the HIV Env glycoprotein, it will be understood that the expression vectors of the invention may also be used for generating furin-cleaved Env-glycoproteins by transient transfection.

In certain embodiments, anti-Env glycoprotein antibodies may be used, for example, to detect, purify, quantify or analyze the HIV Env glycoproteins produced. Desirably, the antibody exhibits specific binding to HIV Env glycoproteins, such as, e.g., BG505 SOSIP.664 trimers or B41 SOSIP.664 trimers. The antibody can either be monoclonal or polyclonal; and can be produced either through immunization of an animal or produced through recombinant DNA technology such as phage display and in vitro mutagenesis or synthesis of the variable regions of the antibody heavy and light chain genes. Polyclonal antibodies include, but are not limited to, human antibodies and humanized antibodies derived from animals such as avian (e.g., chicken), rodent (e.g., rat, mouse, hamster, guinea pig), cow, goat, sheep, rabbit and the like. Monoclonal antibody include antibody derived from a single clone of antibody producing cells including, but not limited to, human cells, and antibodies derived from the cells of other animal types, such as, for example, chicken, rabbit, rat, mouse, hamster, guinea pig, cow, goat, sheep, and the like. Methods of making antibodies are well known in the art (see, e.g., Harlow & Lane, Antibodies, A Laboratory Manual, Cold Spring Harbor, pp. 1-420 (1988)).

Env glycoproteins produced according to the invention can be isolated and purified using methods known in the art. For example, affinity chromatography employing HIV Env glycoprotein ligands and/or anti-Env glycoprotein antibodies can be used to purify the HIV Env glycoproteins. Affinity chromatography can be used alone or in conjunction with ion-exchange, molecular sizing, or HPLC chromatographic techniques. Such chromatographic approaches can be performed using columns or in batch formats, which are well known in the art. In a preferred embodiment, the Env glycoproteins are purified using bNAb 2G12-affinity chromatography followed by size exclusion chromatography (SEC) on a Superdex 200 26/60 column (GE Healthcare, Little Chalfont, United Kingdom) (see Ringe et al., *Proc. Natl. Acad. Sci. U.S.A.*, 110: 18256-18261 (2013); Sanders et al., *PLoS Pathog.*, 9: e1003618 (2013)).

In another embodiment, the Env glycoproteins are purified on an affinity chromatography column based on the PGT145 bNAb that recognizes a trimer-specific, quaternary epitope (Yasmeen et al., *Retrovirology*, 11: 41 (2014); Sanders et al., *PLoS Pathog.*, 9: e1003618 (2013); Julien et al., *Proc. Natl. Acad. Sci. U.S.A.*, 110: 4351-4356 (2013))) in which PGT145 is coupled to CNBr-activated Sepharose 4B beads (GE Healthcare, Little Chalfont, United Kingdom). The PGT145 affinity column is optionally followed by SEC.

The following examples further illustrate the invention but, of course, should not be construed as in any way limiting its scope.

Example 1

This example demonstrates the design of a vector co-expressing an Env glycoprotein (BG505 SOSIP.664) and furin designated pAM/C BG505.

Complete cleavage of BG505 SOSIP.664 gp140 at the gp120-gp41$_{ECTO}$ juncture is essential for the production of native-like trimers (see e.g., Schulke et al., *J. Virol.*, 76: 7760-7776 (2002), Guttman et al., *J. Virol.*, 87: 11462-11475 (2013), Binley et al., *J. Virol.*, 76: 2606-2616 (2002), Ringe et al., *Proc. Natl. Acad. Sci. U.S.A.*, 110:18256-18261 (2013)). Accordingly, the plasmid pcDNA5/FRT (Invitrogen, Carlsbad, Calif.) was modified to co-express an Env protein (BG505 SOSIP.664 gp140) and furin protease (see FIG. 1). The vector was designed such that different promoters were carefully selected for the env and furin genes to balance their expression, such that furin expression was sufficient to cause efficient Env glycoprotein cleavage without being toxic to host cells. A less potent promoter, EFI Alpha, was chosen to control the expression of furin to reduce the risk of cytotoxicity. A more potent promoter, CMV, was chosen to control Env glycoprotein expression (to maximize trimer production).

To prepare the vector, the complete BG505 SOSIP.664 gp140 env gene was cloned into pcDNA5/FRT plasmid vector between the HindIII and NotI sites, under the control of the CMV promoter to promote high-level constitutive Env glycoprotein expression. The EF1 Alpha promoter, the furin protease gene, and a synthetic Poly A modeled from the HSV Thymidine Kinase Poly A (New England BioLabs, Ipswich, Mass.) were also inserted (see FIG. 1 depicting insertion sites). The nucleotide sequence of this vector, designated pAM/C BG505 or pcDNA-FRT BG505 furin A, is provided as SEQ ID NO: 7.

This example explains the design of a vector expressing an Env glycoprotein consistent with the invention.

Example 2

This example demonstrates the selection and propagation of stable 293T and CHO cell lines expressing BG505 SOSIP.664 gp140.

Figure 2:
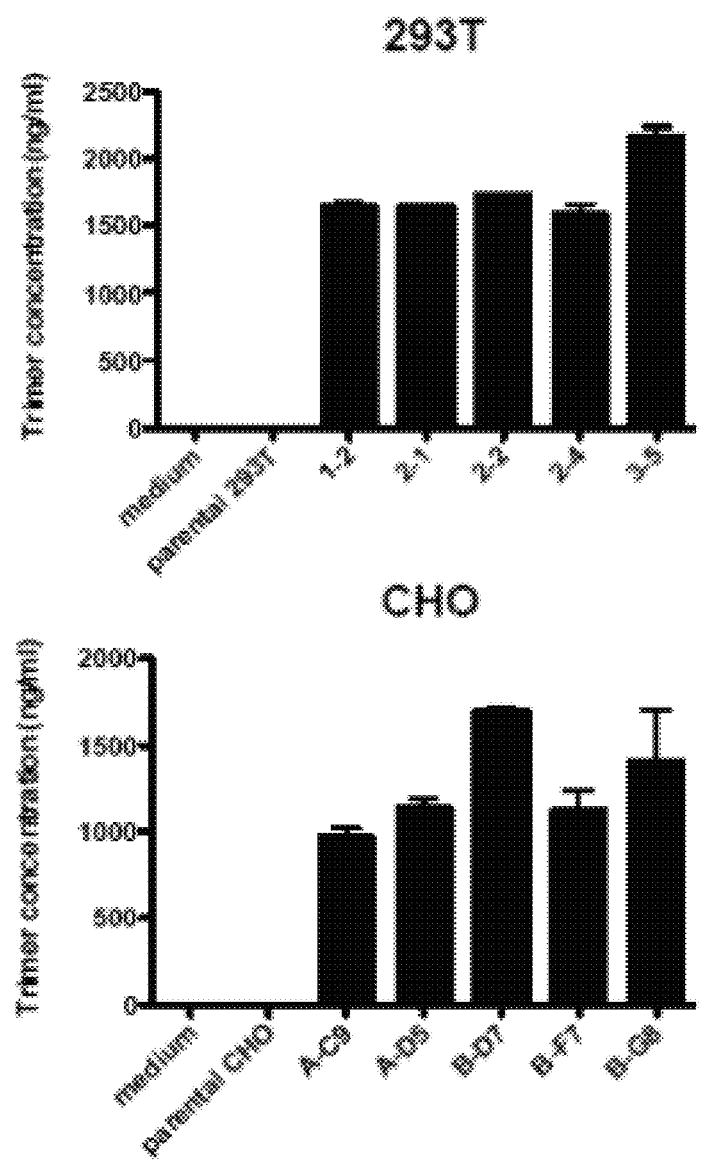
FIG. 2 is comprised of two bar graphs depicting secretion of BG505 SOSIP.664 gp140 trimers by 293T and CHO cell clones. The trimer concentrations in the culture supernatants were determined by ELISA using 2G12 and bio-PGT145.

The pAM/C BG505 vector (see Example 1) was co-transfected with vector pOG44, which encodes the Flp recombinase that mediates integration of the pcDNA5/FRT vector into the FRT site of Flp-In™ cells (Invitrogen, Carlsbad, Calif.). Briefly, the Flp-In™ system allows a gene (or genes) of interest to be inserted into the genome of mammalian cells in an Flp recombinase-dependent manner (pcDNA™5/FRT Vector, Instruction Manual, Invitrogen (2012). Using this system, four potentially stable preliminary cell lines were obtained: 293T lines (designated 13 and 15) and CHO lines (designated A and B). To eliminate the possibility that these initial lines were non-isogenic (i.e., genetically mixed), limiting dilution was performed on the 293T line 13 and CHO lines A and B. These three lines were selected for limiting dilution, as they consistently expressed the highest Env glycoprotein levels relative to parental controls based on a dot blot assay using MAb 2G12. Limiting dilution resulted in 32 potential 293T cell clones and 10 potential CHO cell clones. FITC-labeled MAb 2G12 (FITC-2G12) and fluorescence activated cell sorting (FACS) was used to assess Env expression and clonality. This procedure identified 293T clone 13 #3-5 and CHO clone B-D7 as the highest-expressing clones for further propagation. An ELISA based on 2G12 capture of Env proteins followed by detection of trimers with biotinylated MAb PGT145 (bio-PGT145) confirmed that culture supernatants from these clones contained the highest quantities of trimers: 2.1 µg/ml for 293T clone 13 #3-5 and 1.7 µg/ml for CHO clone B-D7, as shown in FIG. 2. Fluorescent microscopy was also used to confirm stable cell clones. Cells were grown in an 8-well chamber slide, treated with Brefeldin A, fixed, permeabilized, and stained for Env (FITC-2G12) or nuclear DNA (DAPI). The results showed that Env proteins accumulated within the cell for both these clones, but were absent from the parental controls.

These results demonstrate a method for selecting and propagating cells stably expressing the Env glycoprotein and confirm that the desired protein accumulates within selected stable clones.

Example 3

This example demonstrates that selected cell lines expressing BG505 SOSIP.664 gp140 are capable of sustained intracellular Env glycoprotein expression.

Intracellular BG505 SOSIP.664 expression was visually monitored with continued passage of the 293T 13#3-5 and CHO B-D7 stable cell lines. The fixed and permeabilized cells were stained with FITC-2G12 (20 µg/ml) after culture for 6 hours in the presence of Brefeldin A. MFI (mean fluorescence intensity) values for the Env-expressing cells were determined, and parental cells served as negative controls.

After initial seeding, approximately constant levels of intracellular Env glycoprotein (as determined by ELISA) were detected during ten subsequent passages (P1-10, one passage every 4 days) of the 293T clone 13 #3-5 and the CHO clone B-D7. This indicated that both lines were stable and not prone to genetic instability (see FIG. 3).

Figure 3:
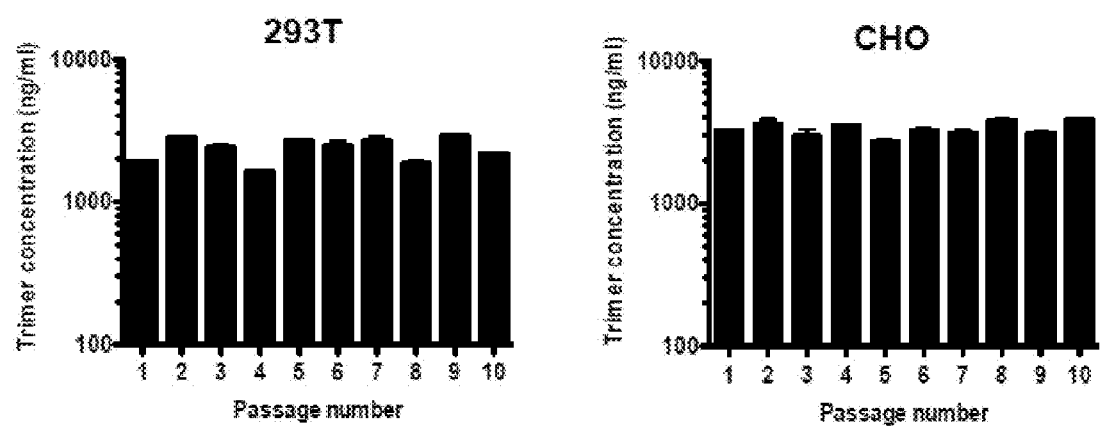
FIG. 3 is comprised of two bar graphs depicting the results of ELISA assays detecting the concentration of BG505 SOSIP.664 gp140 trimers throughout the culture period for 293T and CHO cell clones.
Figure 4:
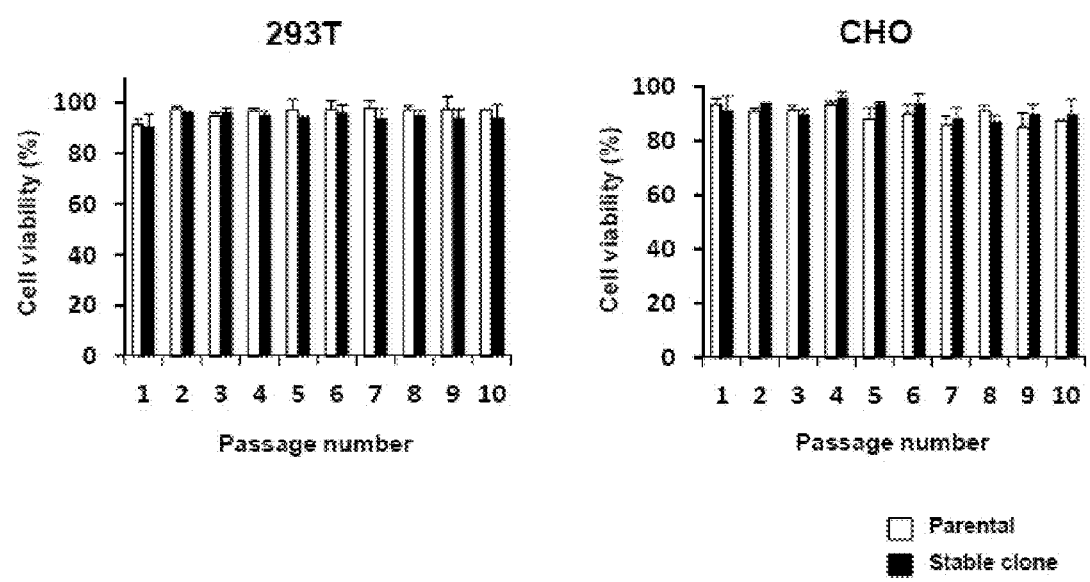
FIG. 4 is comprised of two bar graphs depicting data on the viability of stable cell clones during passage. The cells were stained with trypan blue, with the percentage of viable cells (parental vs. stable) shown as the passage number increases.

The production of BG505 SOSIP.664 gp140 trimers, as judged by ELISA, was also steady over time during passages 1 through 10, with yields in the range of 2 and 3 µg/ml of supernatant for the 293T and CHO cell clones, respectively (FIG. 3). Cell viability (parental vs. stable cell lines) was 91-98% vs. 91-96% for 293T, and 86-95% vs. 87-94% for CHO, throughout the culture period, implying that neither the Env glycoprotein nor furin was cytotoxic to these lines (FIG. 4). Overall, the two stable cell lines could be passaged for five weeks without any observable reduction in Env expression or cell viability. The BG505 SOSIP.664 trimers can, therefore, be produced by the same batch of cells for at least this period after initial seeding, and probably far longer.

This example demonstrates that the inventive methods result in sustained intracellular Env expression in stable 293T and CHO cell lines.

Example 4

This example describes the biochemical characterization of BG505 SOSIP.664 gp140 trimers from 293T and CHO stable cell lines. The quantity and quality of the trimers produced by the stable cell lines were compared with trimers obtained from transiently transfected 293T and CHO cells.

Figure 6:
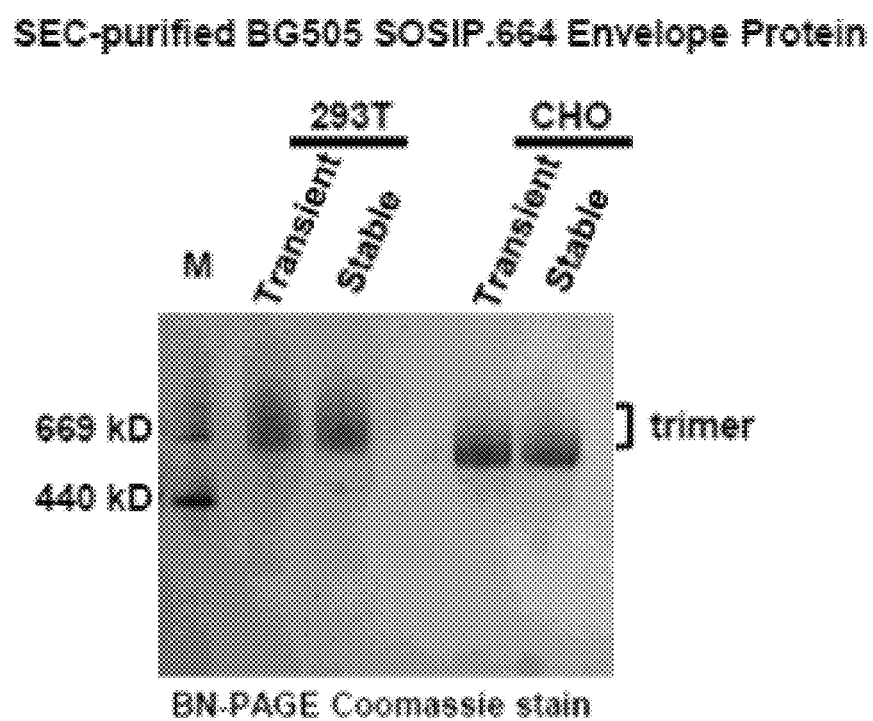
FIG. 6 is a blot depicting the results of a BN-PAGE analysis similar to that of FIG. 5, but of size exclusion chromatography (SEC)-purified trimers.

In all cases, the trimers were purified by 2G12-affinity chromatography followed by size exclusion chromatography (SEC) (see Ringe et al., *Proc. Natl. Acad. Sci. U.S.A.*, 110: 18256-18261 (2013); and Sanders et al., *PLoS Pathog.*, 9: e1003618 (2013)). A Coomassie blue-stained native (BN-PAGE) gel showed that the 2G12-enriched Env glycoproteins were mostly trimeric, with only modest amounts of dimers and/or monomers visible, as shown in FIG. 5. The trimer fractions were then purified by SEC. Gel-electrophoretic analyses under native conditions (BN-PAGE, followed by Coomassie blue staining) showed that the purities of the different trimer preparations (cell lines vs. transient transfection) were indistinguishable, as shown in FIG. 6. The CHO cell-derived trimers migrated slightly more quickly than their 293T counterparts, probably reflecting subtle, cell-dependent differences in glycan profiles that affect mobility during electrophoresis (see FIG. 6).

The yield of purified trimers from the 293T stable cell line was 12 mg (range 10-15 mg) per $1\times10^9$ cells, which is 10-fold greater than when the same number of 293T cells were transiently transfected (range 1.25-1.5 mg) (Table 1). For the stable CHO cell line vs. transiently transfected CHO cells, the corresponding values were 12 mg (range 10-15 mg) and 0.375 mg (range 0.25-0.5 mg), which represents a ~32-fold differential.

Figure 7:
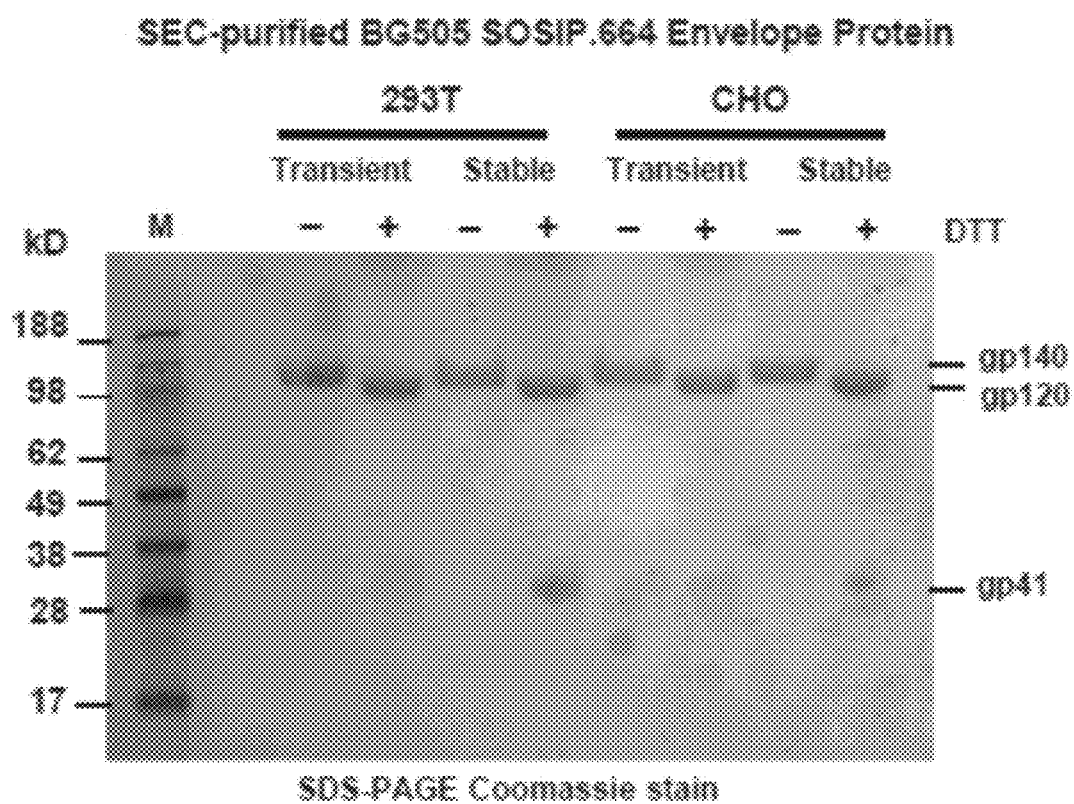
FIG. 7 is a blot depicting the results of an SDS-PAGE analysis of SEC-purified BG505 SOSIP.664 trimers, under non-reducing (−DTT) and reducing (+DTT) conditions, followed by Coomassie blue staining. Cleavage of gp120 from $gp41_{ECTO}$ is assessed by the conversion of the gp140 band to gp120 in the presence of DTT. The released $gp41_{ECTO}$ subunit is not always stained strongly.

The various SEC-purified BG505 SOSIP.664 trimer preparations were fully cleaved. As confirmation, when the reducing agent dithiothreitol (DTT) was included in SDS-PAGE gels, the gp140 proteins dissociated into their gp120 and $gp41_{ECTO}$ subunits, as shown in FIG. 7. Note that the $gp41_{ECTO}$ fragments stained poorly and were not always visible.

Figure 8:
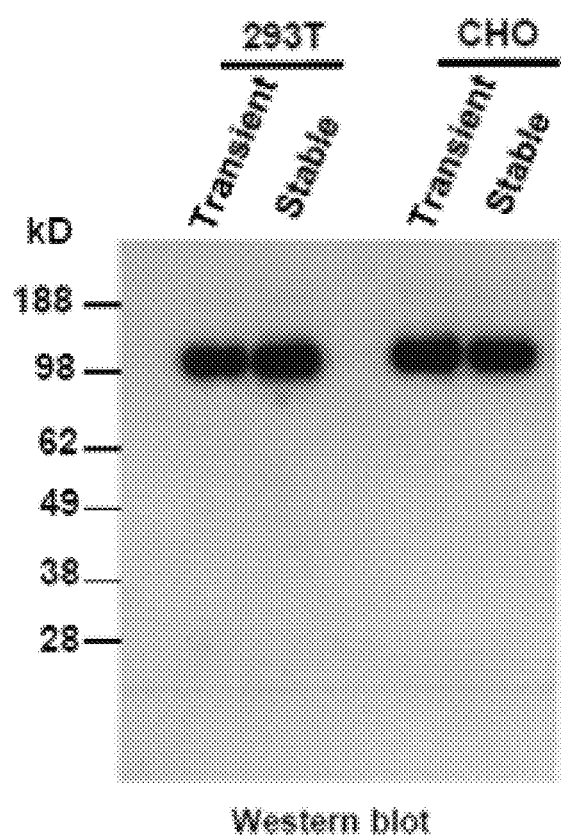
FIG. 8 is a blot depicting the results of a reducing SDS-PAGE analysis to assess the quality of SEC-purified BG505 SOSIP.664 trimers. The trimers were probed with the anti-gp120 MAb, ARP 3119. No Env glycoprotein degradation products arising from V3-clipping or other proteolysis events are visible.

The purified trimers were next analyzed on a reducing SDS-PAGE gel followed by western blotting, with the goal of identifying whether any proteolytic degradation events occur during production or purification, as shown in FIG. 8. The detection MAb, ARP 3119, binds to a well-conserved, linear epitope within the N-terminal half of gp120. The antibody recognizes the 70-kDa (but not the 50-kDa) fragment that is produced when monomeric MN gp120 is clipped by proteases within the V3 region. When the BG505 SOSIP.664 trimer blots were probed with ARP 3119, only a 120-kDa band (i.e., gp120) was detected, with no degradation products visible (see FIG. 9).

Figure 9:
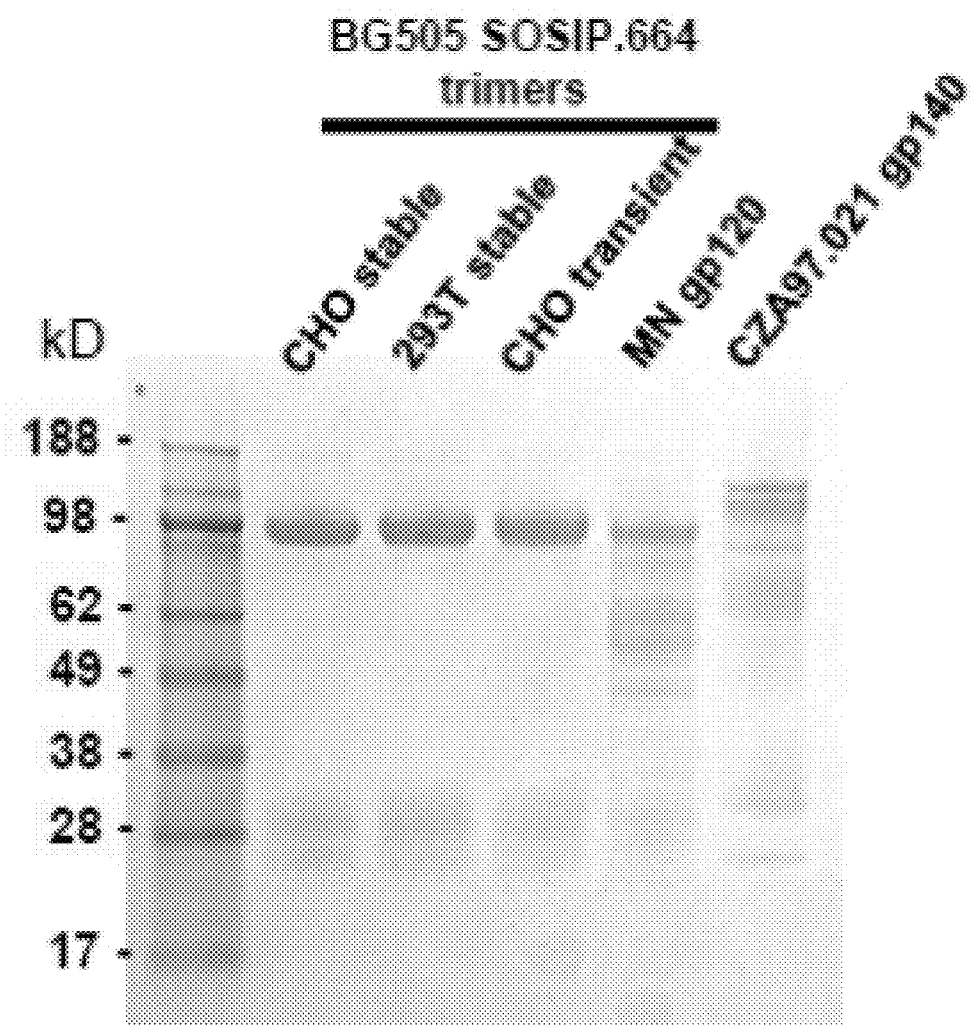
FIG. 9 is a blot depicting the results of a reducing SDS-PAGE analysis of SEC-purified BG505 SOSIP.664 gp140 trimers and comparator Env proteins, followed by Coomassie blue staining. The comparator proteins were also SEC-purified to yield the 120-kDa fraction for MN gp120 and the "trimer" fraction (i.e., proteins containing three gp120 and three $gp41_{ECTO}$ subunits) for uncleaved CZA97.012 gp140. Multiple degradation and/or aggregation products derived from MN gp120 and CZA97.012 gp140 are visible, but none from the BG505 SOSIP.664 trimers.
Figure 10:
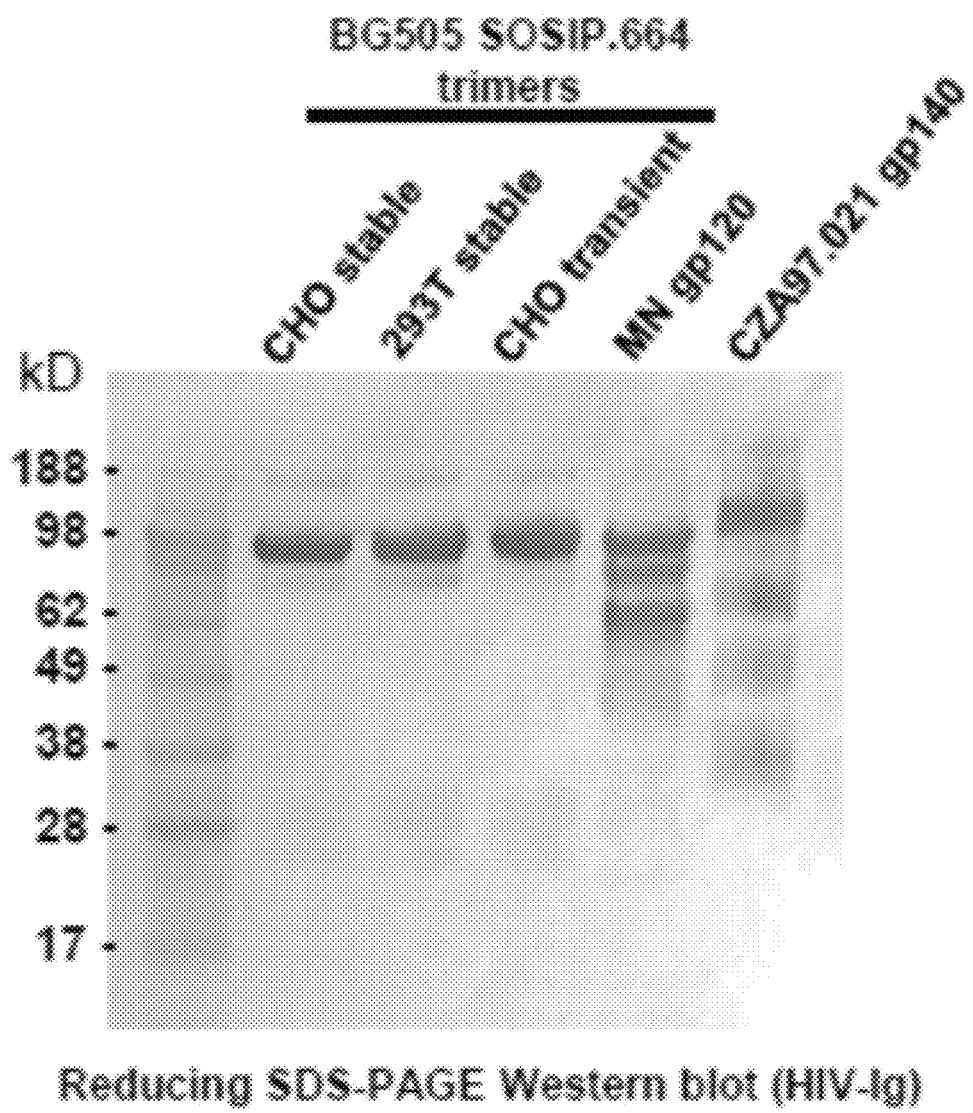
FIG. 10 is a blot depicting the results of a Western blot analysis of the same gel shown in FIG. 9. Here, the detection antibodies were a pool (1:1:1) of polyclonal HIV-Igs derived from subtype A, B and C infections. The various aggregates or degradation products seen in (E) are Env-based.

To seek any Env fragments that might escape detection by ARP 3119, a similar reducing SDS-PAGE and Western blotting analysis was performed. Here, the blots were probed with polyclonal HIV-Ig (FIGS. 9 and 10). Two other types of Env protein were included as positive controls: a monomeric gp120 (MN) and an uncleaved gp140 that contained three gp120 and three $gp41_{ECTO}$ subunits (CZA97.012). The controls were known to be vulnerable to proteolytic degradation (see Guttman et al., *J. Virol.*, 87: 11462-11475 (2013); Ringe et al., *Proc. Natl. Acad. Sci. U.S.A.*, 110:18256-18261 (2013); Schulz et al., *AIDS Res. Hum. Retroviruses*, 9:159-166 (1993); and Clements et al., *AIDS Res. Hum. Retroviruses*, 7: 3-16 (1991)). The BG505 SOSIP.664 trimers were derived from subtype A, the gp120 protein was derived from subtype B, and the uncleaved gp140, was derived from subtype C (see Kovacs et al., *Proc. Natl. Acad. Sci. U.S.A.*, 109: 12111-12116 (2012)). Accordingly, an HIV-Ig pool was used based on sera from different individuals infected with viruses from all three subtypes. The gp120 and gp140 proteins were SEC-purified and each migrated as a single band of appropriate size when analyzed by BN-PAGE and Coomassie blue staining.

The Coomassie blue-stained, reducing SDS-PAGE gel again revealed no degradation products of the BG505 SOSIP.664 trimers; the major band corresponded to the gp120 subunit and a less well stained, smaller band corresponded to the $gp41_{ECTO}$ moiety. In contrast, multiple degradation products were clearly visible in the SEC-purified monomeric gp120 and uncleaved gp140 preparations. The dominant bands from the gp120 monomers were the characteristic 70 kDa and 50 kDa fragments arising from V3 clipping. However, additional, unknown fragments of the uncleaved gp140 were also present, as well as high molecular weight bands corresponding to proteins that spontaneously aggregated after SEC-purification (FIG. 9). These observations were reinforced by Western blots, which confirmed that the various additional gp120- or gp140-derived bands were Env proteins. Again, however, there were no signs of degradation or aggregation with the various cell sources of BG505 SOSIP.664 trimers, as shown in FIG. 10.

The results described above demonstrate that the cell line-derived BG505 SOSIP.664 trimers are not degraded by proteases, including but not limited to proteases that clip the V3 region to yield characteristic 70 kDa and 50 kDa fragments on reducing SDS-PAGE gels and Western blots (see FIGS. 9-10) (Schulz et al., *AIDS Res. Hum. Retroviruses*, 9: 159-166 (1993); and Clements et al., *AIDS Res. Hum. Retroviruses*, 7: 3-16 (1991)18, 19). In contrast, the monomeric gp120 (MN) and the uncleaved gp140 (CZA97.012) were highly vulnerable to proteolytic degradation, including but in the latter case not limited to, V3 clipping. The uncleaved gp140 also formed aggregates even after the fraction corresponding to three gp120 and three $gp41_{ECTO}$ subunits was first SEC-purified (FIGS. 9-10). The resistance of the BG505 SOSIP.664 trimers to proteolytic degradation may be the result of the BG505 V3 sequence not being particularly vulnerable to clipping compared to other Env genotypes. For example, no signs of V3 clipping were observed when making monomeric BG505 gp120 proteins by transient transfection when, under the same conditions, MN gp120 is badly degraded. However, there are also structural considerations; the SOSIP.664 trimers are compact entities in which potentially vulnerable scissile sites, particularly V3, are inaccessible to proteases (Julien et al., *Science,* 342: 1477-1483 (2013); Lyumkis et al., *Science,* 342: 1484-1490 (2013)). In contrast, V3 and other protease-sensitive regions are more exposed on both gp120 monomers and uncleaved gp140s. The latter invariably adopt splayed out, non-native shapes with three individual gp120 subunits dangling freely from a central gp41$_{ECTO}$ 6-helix-bundle, conformations in which various sites, including V3, are exposed to protease attack (Guttman et al., *J. Virol.,* 87: 11462-11475 (2013); Ringe et al., *Proc. Natl. Acad. Sci. U.S.A.,* 110: 18256-18261 (2013)). In addition, the uncleaved gp140 proteins formed aggregates post-purification. This probably arose from the exposure of hydrophobic sites within gp41$_{ECTO}$. The native-like, cleaved BG505 SOSIP.664 trimers do not form such aggregates.

The results of this example confirm that the inventive methods result in high quantities of properly cleaved, high quality, Env glycoprotein trimers.

Example 5

This example describes surface plasmon resonance and ELISA analysis of BG505 SOSIP.664 gp140 trimers produced from stable 293T and CHO cell lines.

The BG505 SOSIP.664 gp140 trimers produced by the permanent cell lines do not contain a D7324-epitope or His-tags. Accordingly, surface plasmon resonance (SPR) and ELISA methods were developed that are suitable for use with non-tagged trimers derived from both the permanent 293T and CHO cell lines and, for comparison, trimers made by transient transfection.

Figure 11:
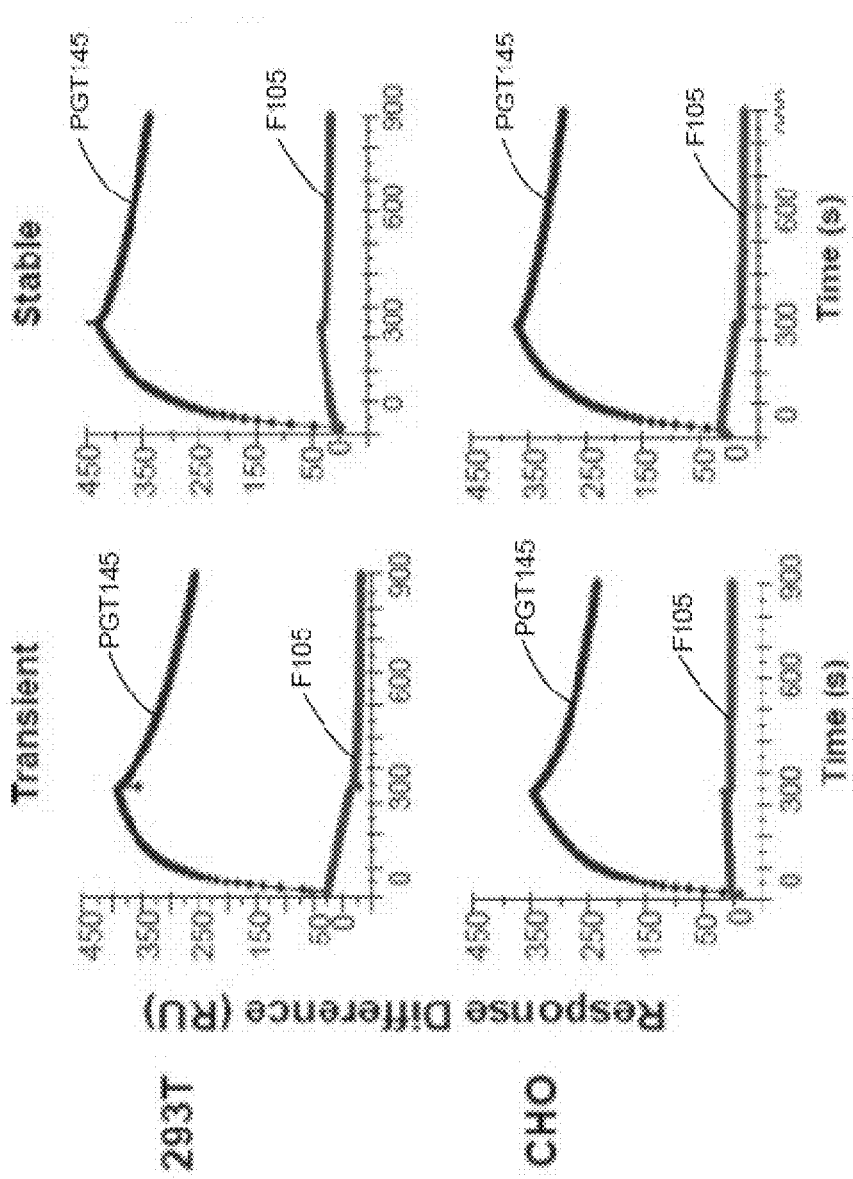
FIG. 11 is a set of graphs that present data on the antigenicity of cell line-derived BG505 SOSIP.664 gp140 trimers. Presented are SPR sensorgrams for the PGT145 bNAb and the F105 non-NAb. Each MAb was captured onto the chip by an immobilized anti-Fc Ab, and the binding of BG505 SOSIP.664 gp140 trimers (200 nM) from the various cell sources was recorded as response difference (RU) after background correction: PGT145 bound strongly and similarly to the trimers of different origin, but F105 binding was undetectable. Each curve represents one of two similar replicates.

For SPR, anti-Env glycoprotein MAbs were immobilized on CM5 chips and the purified BG505 SOSIP.664 gp140 trimers were flowed over them. Binding was recorded as the response difference (RU). bNAb PGT145, immobilized to a quaternary structure-dependent epitope, bound strongly to the trimers, as shown in FIG. 11. In contrast, the non-NAb F105 bound only minimally, which is consistent with the occlusion of its CD4bs epitope on native-like trimers (Sanders et al., *PLoS Pathog.,* 9: e1003618 (2013); Walker et al., *Nature,* 477: 466-470 (2011)). Of note is that the binding profiles obtained for the two MAbs were independent of the cell source of the trimers (FIG. 11).

Figure 12:
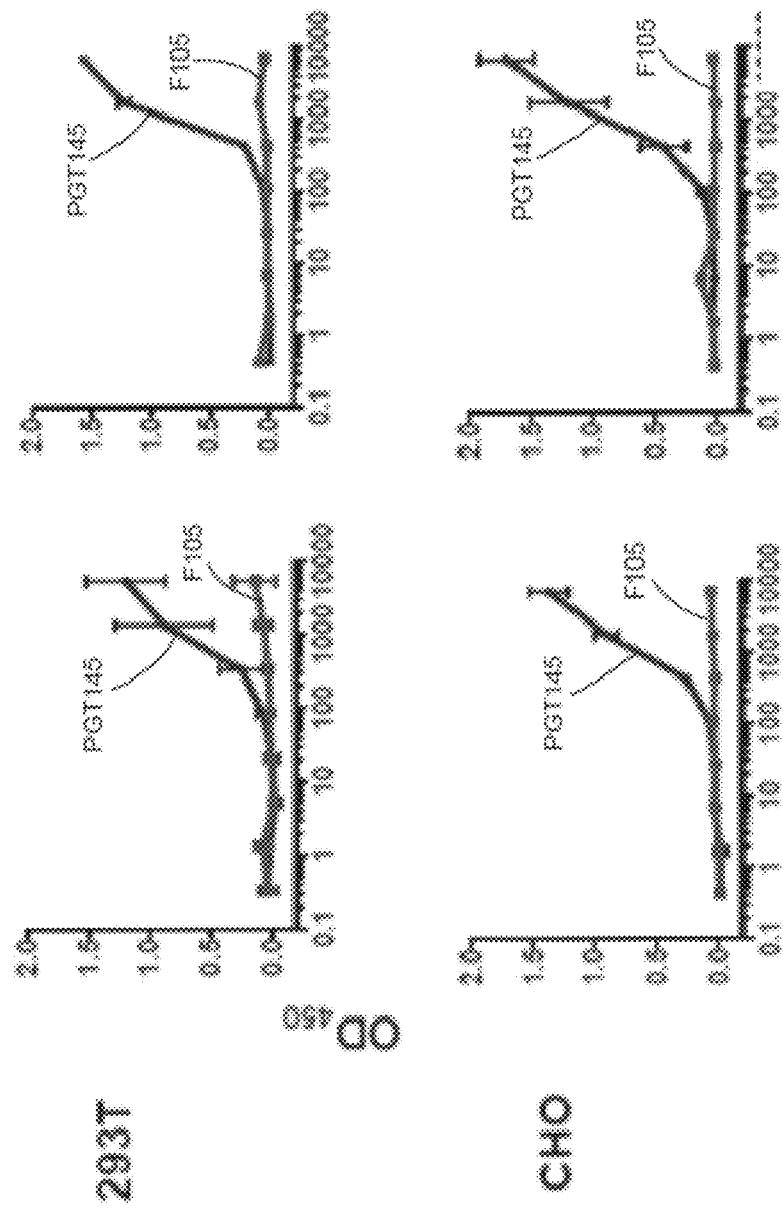
FIG. 12 is a set of graphs depicting representative binding curves in the 2G12-capture ELISA for the same PGT145 bNAb and F105 non-NAb to BG505 SOSIP.664 gp140 trimers referenced in FIG. 11 from the 293T and CHO cell lines. The plotted OD values have been background corrected (i.e., with no gp120 present). Each curve represents one of two similar replicates. Similar data were obtained in three experiments of the same design.

The ELISA assay involved trimer capture to the solid phase via absorbed bNAb 2G12. This was followed by detection using biotin-labeled versions of the same PGT145 or F105 MAbs used in the SPR assay. As with the SPR system, an appropriate measure of structural authenticity for the trimers is strong PGT145 reactivity combined with low binding of F105. Again, irrespective of the trimer source, PGT145 bound efficiently in the 2G12-capture ELISA whereas F105 was completely non-reactive (FIG. 12).

These results confirm that the Env glycoprotein trimers obtained from the stable 293T and CHO cell lines are comparable to trimers produced by transient transfection.

Example 6

This example describes the use of Electron microscopy to image BG505 SOSIP.664 gp140 trimers produced from stable 293T and CHO cell lines.

Figure 13:
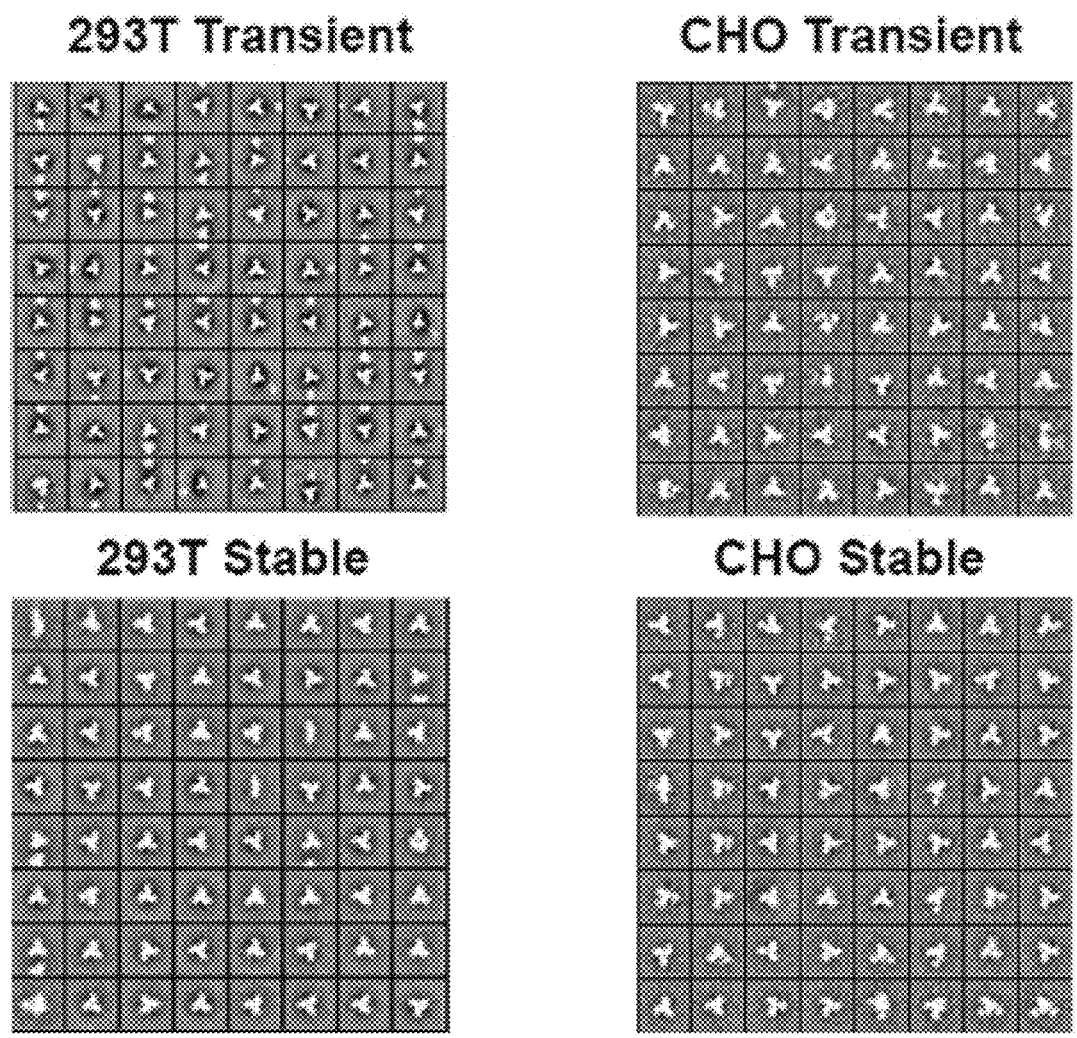
FIG. 13 depicts Negative stain EM images and DSC traces for BG505 SOSIP.664 gp140 trimers produced by 293T and CHO cells. Reference-free 2D class averages are shown for trimers from transiently transfected or stable 293T and CHO cell lines, as indicated.

The different preparations of purified trimers were viewed by negative-stain EM, and the reference-free 2D class averages were examined to determine their overall morphology. The trimers from both cell lines had the same consistently native-like appearance as those derived by transient transfection (see FIG. 13) (see Sanders et al., *PLoS Pathog.,* 9: e1003618 (2013)). The percentages of native-like trimers varied in the range of 81-100%, and were usually somewhat higher for 293T cell-derived trimers (90-100%) than CHO (80-90%). However, native-like trimer percentages in this range (80-100%) are within experimental error for this method. Accordingly, the data demonstrates that trimers from both the 293T and CHO stable lines adopt a single native-like configuration that is indistinguishable, at this level of resolution, from the transient transfection products used to derive high-resolution cryo-EM and X-ray structures (see Julien et al., *Science,* 342: 1477-1483 (2013); and Lyumkis et al., *Science,* 342:1484-1490 (2013)).

The results of this example further confirm that the Env glycoprotein trimers obtained from the stable 293T and CHO cell lines are comparable to trimers produced by transient transfection.

Example 7

This example describes the use of a differential scanning calorimetry (DSC) assay to analyze trimers derived from stable 293T and CHO cells.

Figure 14:
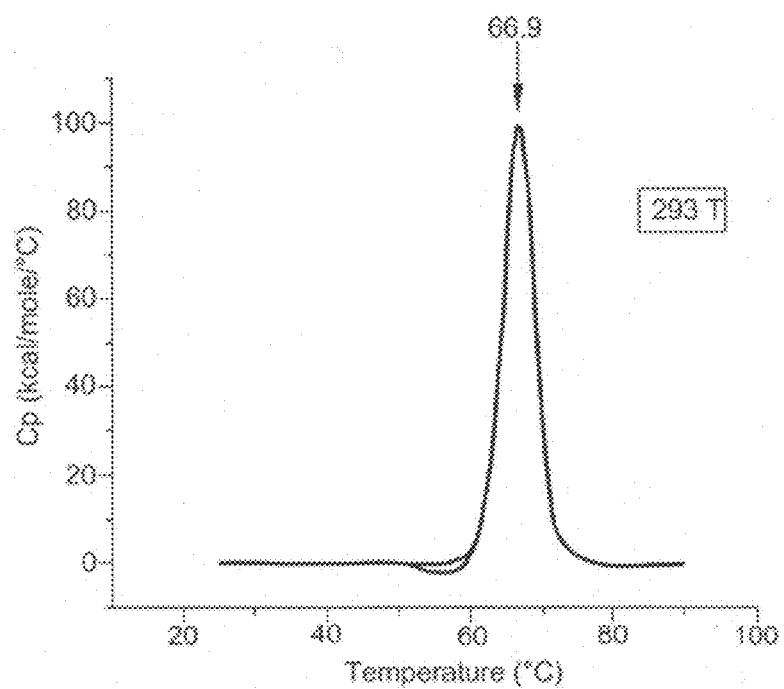
FIG. 14 is comprised of two graphs depicting thermal denaturation profiles of BG505 SOSIP.664 trimers from the stable 293T cell line (top panel) and the stable CHO cell line (bottom panel).
Figure 14:
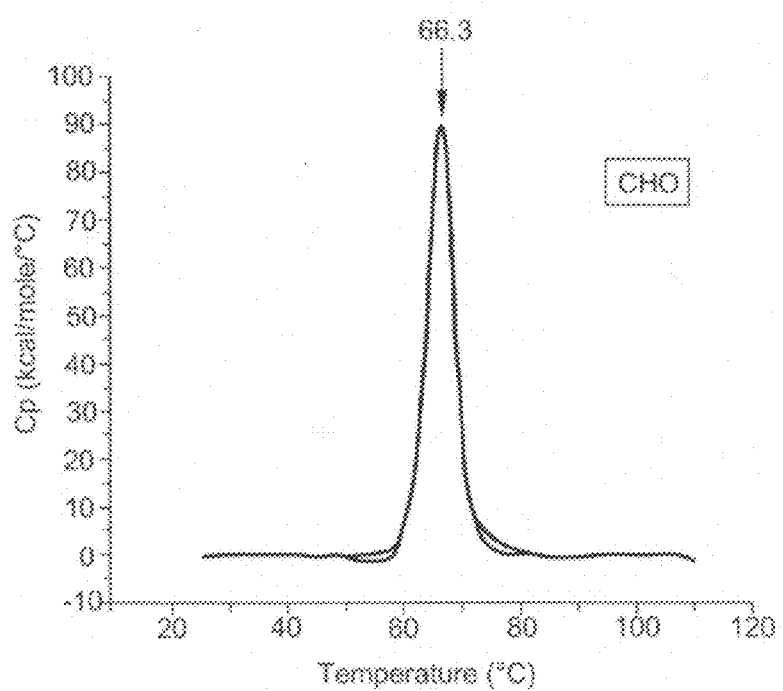

In the DSC assay, trimers produced in the stable 293T and CHO cell lines underwent a single, sharp thermal transition at 66.9° C. and 66.3° C., respectively (FIG. 14). These values are comparable to those observed at 68.1° C. for trimers produced by transient transfection of 293T cells (Sanders et al., *PLoS Pathog.,* 9: e1003618 (2013)), and 67.9° C. for trimers produced by transient transfection of 293S cells (Julien et al., *Proc. Natl. Acad. Sci. U.S.A.,* 110: 4351-4356 (2013)).

The results of this example further confirm that the Env glycoprotein trimers obtained from the stable 293T and CHO cell lines are comparable to trimers produced by transient transfection.

Example 8

This example describes the modification of env genes derived from HIV subtype B and Subtype C.

The BG505 SOSIP.664 gp140 trimers discussed above are derived from HIV subtype A. The B41 env gene, discussed in this example, is an env gene derived from a subtype B founder virus isolated from a HIV-1-infected serial plasma donor. It is formally designated 9032-08.A1.4685 and its GenBank accession number is EU576114 (Wilen et al., *J. Virol.,* 85: 8514-8527 (2011)). To prepare a SOSIP.664 gp140 construct based on B41, the following sequence changes were introduced to the B41 gene (HxB2 numbering system):
   a. A501C and T605C—resulting in a gp120-gp41$_{ECTO}$ disulfide bond (see Binley et al., *J. Virol.,* 74: 627-643 (2000));
   b. I559P in gp41$_{ECTO}$—a trimer-stabilizing modification (see Sanders et al., *J. Virol.,* 76: 8875-8889 (2002));
   c. REKR (SEQ ID NO: 9) to RRRRRR (SEQ ID NO: 10) in gp120—for cleavage enhancement (see Binley et al., *J. Virol.,* 76: 2606-2616 (2002));
   d. A TPA leader peptide was added to increase gene expression (see Sanders et al., *PLoS Pathog.,* 9: e1003618 (2013); and Sellhorn et al., *Vaccine,* 28:430-436 (2009)); and A stop codon was added at gp41$_{ECTO}$ residue 664 to improve homogeneity and solubility (see Khayat et al., *J. Virol.*, 87: 9865-9872 (2013); and Klasse et al., *J. Virol.*, 87: 9873-9885 (2013)).

The resulting, codon-optimized B41 SOSIP.664 env gene was obtained from Genscript (Piscataway, N.J.) and cloned into pPPI4 using PstI and NotI (see Binley et. al., J. Virol 74:627-643 (2000)). The encoded HIV glycoprotein trimers were designated B41 SOSIP.664. Trimer variants containing a D7324 epitope-tag sequence at the C-terminus of gp41$_{ECTO}$ were also made, by adding the sequence GSAPT-KAKRRVVQREKR (SEQ ID NO: 8) after residue 664 in gp41$_{ECTO}$ and prior to the stop codon (see Sanders et al., *PLoS Pathog.*, 9: e1003618 (2013)). This trimer was designated B41 SOSIP.664-D7324.

Additionally, SOSIP modifications such as those outlined above were applied to an env gene derived from a Subtype C HIV virus.

A monomeric B41 gp120 protein was also prepared based on the same sequence with the following alterations:
 a. introducing a stop codon into the SOSIP.664 construct at residue 512;
 b. reverting the optimized cleavage site to wild type (RRRRRR (SEQ ID NO: 10)→REKR (SEQ ID NO: 9) at residues 508-511);
reverting the A501C change and making an A500K substitution to optimize the D7324 epitope that is present in the C5 domain at the gp120 C-terminus.

This example demonstrates methods for making SOSIP modifications to an Env glycoprotein gene derived from different subtypes of HIV. The example further demonstrates the preparation of a monomeric gp120 protein.

Example 9

This example describes the expression of B41 SOSIP.664 by transient transfection.

B41 SOSIP.664 Env glycoproteins were expressed in wild type, adherent HEK293T ("293T") cells by transient transfection of the B41 SOSIP.664 genes using polyethyleneimine (PEI), essentially as described elsewhere (see Sanders et al., *PLoS Pathog.*, 9: e1003618 (2013); Kirschner et al., *Protein Expr. Purif.*, 48: 61-68 (2006)). The furin gene was co-transfected with all SOSIP.664 trimer-encoding env genes to maximize gp120-gp41$_{ECTO}$ cleavage (see Binley et al., *J. Virol.*, 74: 627-643 (2000); Binley et al., *J. Virol.*, 76: 2606-2616 (2002)). The transfected 293T cells were initially cultured in the presence of 10% fetal calf serum (FCS).

Figure 15:
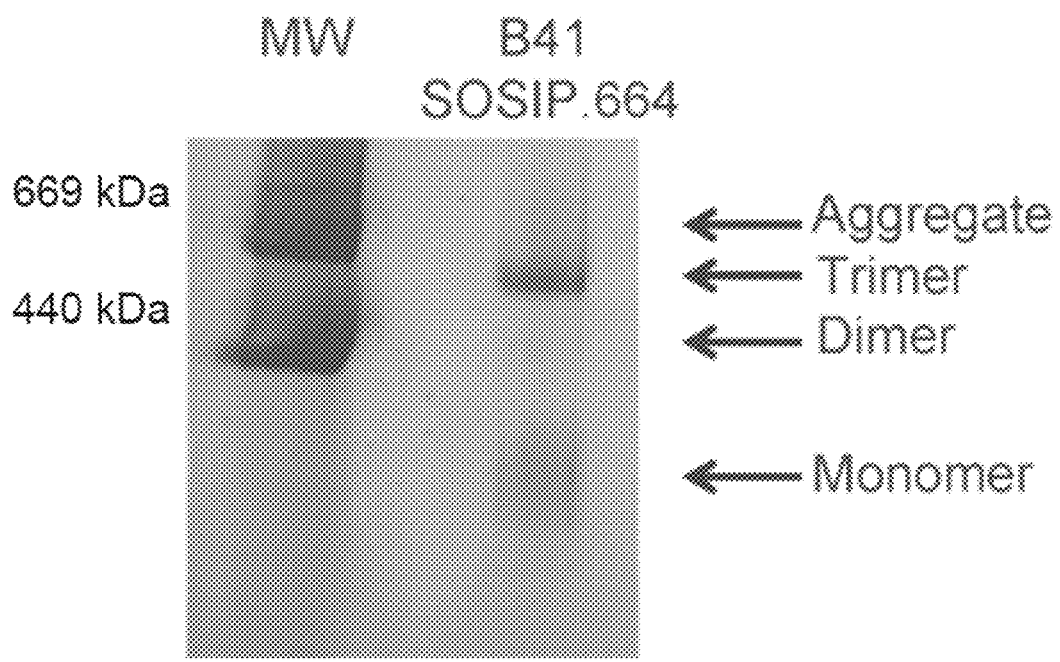
FIG. 15 is a blot that depicts the biochemical characterization of B41 SOSIP.664 trimers via SDS PAGE. The B41 SOSIP.664 env and furin genes were expressed in 293T cells in the presence of 10% FCS. B41 SOSIP.664 Env glycoproteins were purified on a 2G12 affinity column were analyzed on a Coomassie blue-stained BN1103 PAGE gel. The bands corresponding to aggregates (A), trimers (T), dimers (D) and 1104 monomers (M) are indicated. The molecular weight marker proteins (MW) were 1105 thyroglobulin (669 kDa) and ferritin (440 kDa). Comparable results (not-shown) were obtained via SEC (size exclusion chromatography) analysis on a Superdex 200 26/60 column.
Figure 16:
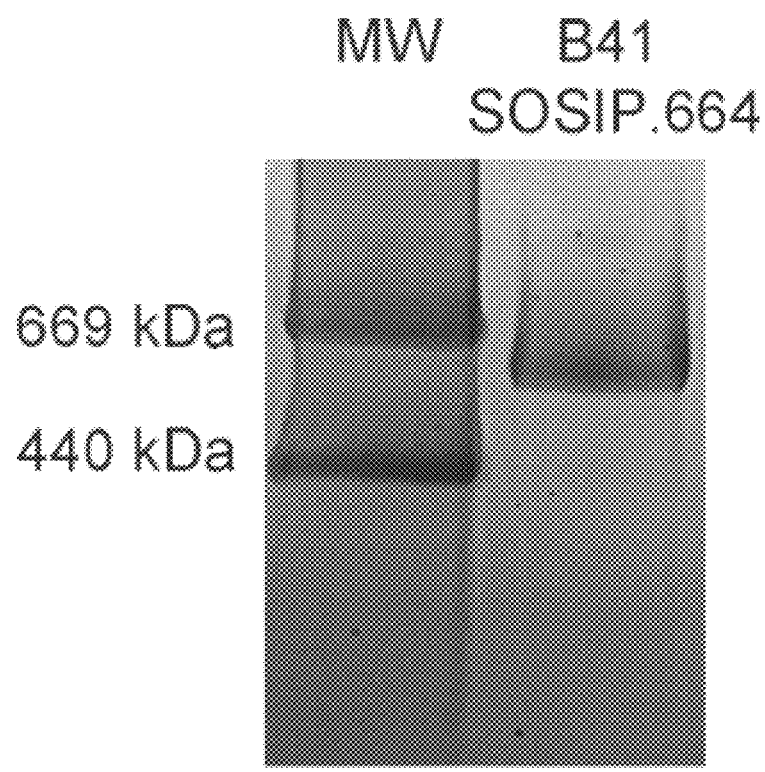
FIG. 16 is a blot that depicts the results of Coomassie blue-stained BN1107 PAGE analysis of B41 SOSIP.664 trimers purified via 2G12/SEC columns.

The secreted B41 SOSIP.664 Env proteins were first affinity-purified using the 2G12 bNAb, followed by SEC via a Superdex 200 26/60 column to isolate trimers. A BN PAGE analysis of the B41 SOSIP.664 Env proteins eluted from the 2G12 column showed that >40% were trimers, while dimers, monomers, and aggregates were each present at relative abundances of ~20%, as shown in FIG. 15. The SEC column removed unwanted Env forms, yielding pure (>95%) trimers (see FIG. 16). A comparative reducing vs. non-reducing SDS-PAGE gel analysis showed that the purified trimers were fully cleaved (>95%) into their gp120 and gp41$_{ECTO}$ subunits (data not shown). These results broadly mirror results observed with BG505 SOSIP.664 trimers (see, e.g., Sanders et al., *PLoS Pathog.*, 9: e1003618 (2013)).

Figure 17:
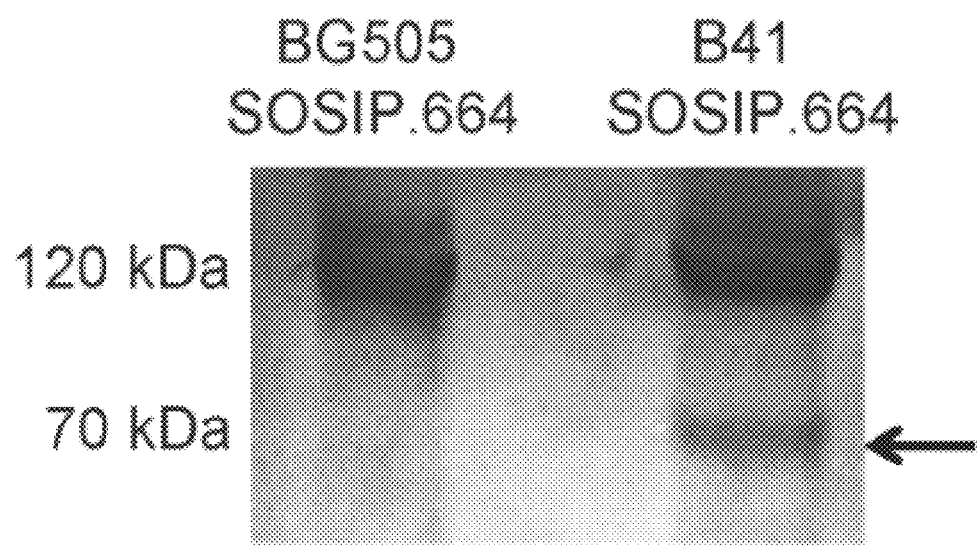
FIG. 17 is a blot that depicts the results of an assay comparing BG505 SOSIP.664 trimers and B41 SOSIP.664 trimers. Both Env proteins were produced in 293T cells in the presence of 10% FCS, purified via 2G12/SEC columns and then analyzed by reduced SDS-PAGE followed by western blotting with MAb ARP3119. The 70-kDa fragment of gp120 that is characteristic of V3-clipping is indicated with an arrow.

However, in contrast with BG505, some degradation products were observed when the B41 SOSIP.664 trimers were analyzed by reducing SDS-PAGE followed by Coomassie blue staining or western blotting (FIG. 17). The anti-gp120 MAb ARP3119 detected a band of ~70 kDa that is characteristically observed when the V3 region of gp120 is proteolytically clipped at a scissile site near the tip of its β-hairpin loop (see Berman et al., *Nature*, 345:622-625 (1990); Clements et al., *AIDS Res. Hum. Retroviruses*, 7: 3-16 (1991); Du et al., *Protein Expr. Purif*, 59: 223-231 (2008)). The other gp120 fragment generated by V3-clipping, a band of approximately 50 kDa, is not recognized by MAb ARP3119. This fragment and other less prominent bands (i.e., other degradation products) were detected when an HIV-Ig (subtype B) preparation was used to probe the blots.

Figure 18:
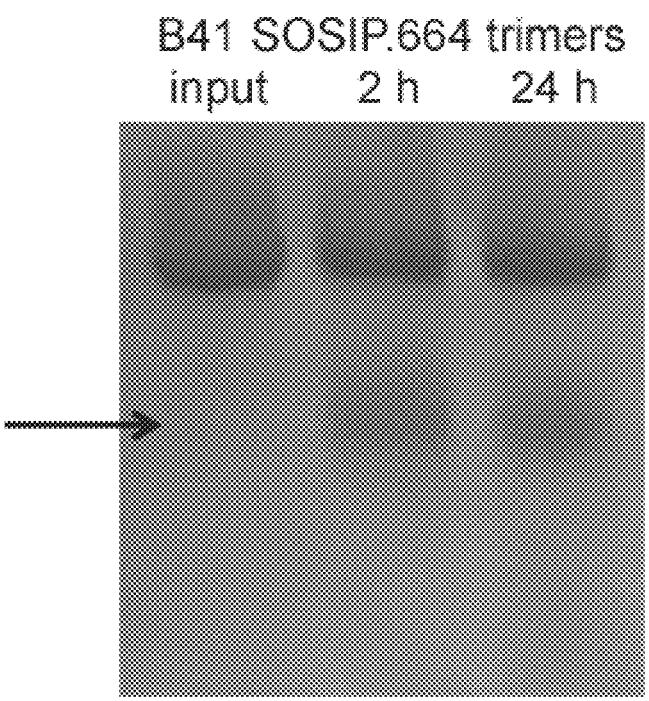
FIG. 18 is a blot that depicts the results of an SDS-PAGE assay. B41 SOSIP.664 trimers were produced in 293F cells in serum-free medium and treated with thrombin (100 μg/ml) for the specified times before analysis by reducing SDS-PAGE and western blotting with MAb ARP3119.

The extent of V3-clipping varied between B41 SOSIP.664 trimer preparations but never exceeded more than ~25%, as judged by the relative intensities of the 70 kDa and 120 kDa bands in semi-quantitative assessments. In contrast, monomeric B41 gp120 proteins were much more extensively V3-clipped (usually >50%) when produced and analyzed under the same conditions, as shown in FIG. 18. Compared to other subtypes, Env glycoproteins from subtype B are known to be generally quite vulnerable to V3 clipping, because a scissile site for thrombin-family proteases is present in their consensus V3 sequence that is absent from the corresponding non-subtype B consensus sequence (GPGQAF) (see Berman et al., *Nature*, 345:622-625 (1990); Clements et al., *AIDS Res. Hum. Retroviruses*, 7: 3-16 (1991); Du et al., Protein *Expr. Purif.*, 59: 223-231 (2008); and Aggarwal et al., *Abstr. Cell Cul. Eng. XIV Conf.*, abstr. D015 (2014)). A transient opening of the closed form of the B41 SOSIP.664 trimer may expose the V3 region to any proteases present in the cell culture.

To overcome the problem of V3 clipping, B41 SOSIP.664 proteins were subsequently produced by transient transfection of 293F cells in serum-free medium. The resulting trimers, purified by 2G12/SEC columns, were fully intact with no evidence of V3-clipping in a western blot analysis, implying that FCS was indeed the source of the proteolytic activity (FIG. 18). When the non-clipped, 293F cell-derived trimers were treated with thrombin, a sub-population (~20%) became clipped (FIG. 18). Hence, 293F cells do not produce Env glycoprotein variants that are intrinsically resistant to V3-clipping, but rather it is their ability to be cultured in serum-free medium that yields non-clipped B41 gp120 monomers and SOSIP.664 trimers.

The results of this example demonstrate the production and purification of B41 SOSIP.664 trimers by transient transfection, and that decreased serum concentration results in decreased V3-clipping in the trimers.

Example 10

This example describes the preparation of cell lines expressing BG41 SOSIP.664 trimers and cell lines expressing an Env glycoprotein derived from HIV Subtype C.

Figure 19:
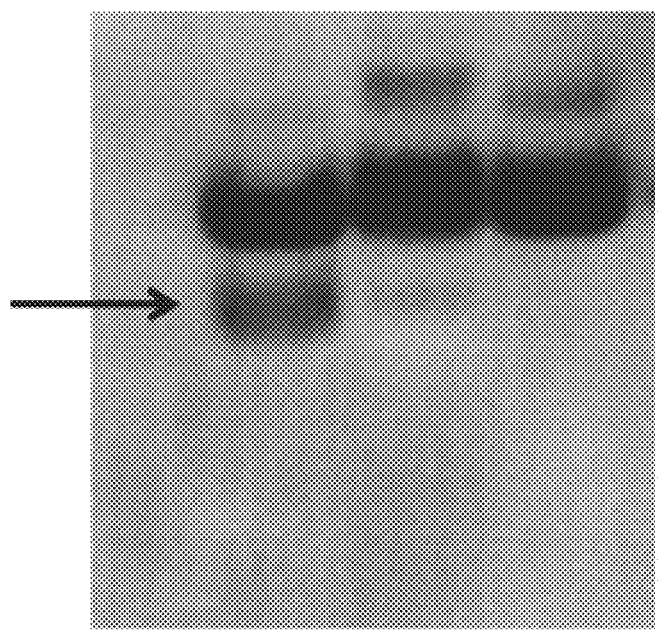
FIG. 19 is a blot that depicts the results of SDS-PAGE analysis of B41 SOSIP.664 trimers. B41 SOSIP.664 trimers were produced (a) transiently in 293T cells in the presence of 10% FCS, (b) in stable CHO cell lines in the presence of 1% FCS, or (c) transiently in 293F cells under serum-free conditions. Trimers were purified via the 2G12 affinity column and SEC, and then analyzed by SDS-PAGE and western blotting with MAb ARP3119 as shown. The 70-kDa fragment of gp120 that is characteristic of V3-clipping is indicated with an arrow.

CHO and 293T cell lines that produce B41 SOSIP.664 trimers were generated using the methods described in Examples 2 and 3. In this regard, a pcDNA5/FRT vector (Invitrogen, Carlsbad, Calif.) was modified to co-express an Env protein (in this case B41 SOSIP.664) and furin protease. The initial clones of stably transfected CHO and 293T cells, cultured in 10% FCS, also yielded trimers that were ~20% V3-clipped in the absence of significant cell damage/death. To reduce the extent of V3 clipping, it was necessary to try to adapt the stable lines to grow at lower serum concentrations than the standard culture conditions (i.e., with 10% FCS present). With the stable 293T line, the FCS concentration could only be reduced to 5% without a substantial decrease in cell viability; at 5% FCS, some V3-clipping still occurred. However, the stable CHO cell line could be successfully adapted to 1% serum. The B41 SOSIP.664 trimers produced when this line was cultured in 1% serum were only minimally (<5%) V3-clipped, as shown in FIG. 19. The resultant stable CHO cells were then propagated under hygromycin resistance in PRO-CHO-AT medium (Lonza, Basel, Switzerland) containing 1% FCS.

Using the methods described herein, cell lines were also established that express a SOSIP modified Env glycoprotein derived from a Subtype C HIV virus. To do this, an expression vector was constructed by modifying a pcDNA5/FRT vector (Invitrogen, Carlsbad, Calif.) to co-express the SOSIP modified env gene derived from a Subtype C HIV virus and furin protease.

The results of this example demonstrate that the inventive method can be used to develop stable cell lines expressing BG41 SOSIP trimers, and cell lines expressing Env glycoproteins derived from an HIV Subtype C virus. The results of this example further demonstrate that the method can be optimized to produce high-quality Env glycoproteins by varying concentration of FCS in cell culture.

Example 11

This example describes methods for purifying the B41 SOSIP.664 trimers.

Two methods were used to purify B41 SOSIP.664 trimers (and D7324-tagged variants thereof) from transfection supernatants. In the first procedure, Env proteins were isolated via a bNAb 2G12 affinity column and MgCl$_2$ elution, and the trimer fraction was purified by SEC on a Superdex 200 26/60 column (GE Healthcare, Little Chalfont, United Kingdom) (see Ringe et al., *Proc. Natl. Acad. Sci. U.S.A.*, 110: 18256-18261 (2013); and Sanders et al., *PLoS Pathog.*, 9: e1003618 (2013)).

The second method involved an affinity column based on the PGT145 bNAb that recognizes a trimer-specific, quaternary epitope (Yasmeen et al., *Retrovirology*, 11:41 (2014); Sanders et al., *PLoS Pathog.*, 9: e1003618 (2013); and Julien et al., *Proc. Natl. Acad. Sci. U.S.A.*, 110: 4351-4356 (2013))). PGT145 was coupled to CNBr-activated Sepharose 4B beads (GE Healthcare, Little Chalfont, United Kingdom). Env-containing culture supernatants were flowed through the resulting column, the beads were washed with 2 column volumes of buffer (0.5 M NaCl, 20 mM Tris, pH 8.0), and the bound trimers were eluted using 1 column volume of 3 M MgCl$_2$. The eluted trimers were immediately buffer-exchanged into 75 mM NaCl, 10 mM Tris, pH 8.0, using Snakeskin dialysis tubing (10K MWCO) (Thermo Scientific, Waltham, Mass.). The purified trimers were then concentrated using Vivaspin columns with a 30-kDa cut off (GE Healthcare Little Chalfont, United Kingdom). Trimers eluted from the PGT145 column were then further purified by SEC.

The results of this example demonstrate two methods for purifying an Env glycoprotein.

Example 12

This example describes the use of affinity chromatography to remove V3 clipped B41 SOSIP.664 trimers.

The trimer apex is formed by an association between the V2 and V3 variable regions and is recognized by the PGT145 bNAb. PGT145 is highly specific for native-like, closed trimers and thus does not bind gp120 monomers, gp120-gp41$_{ECTO}$ promoters, or non-native gp140$_{UNC}$ proteins (Yasmeen et al., *Retrovirology*, 11:41 (2014); Sanders et al., *PLoS Pathog.*, 9: e1003618 (2013); and Julien et al., *Proc. Natl. Acad. Sci. U.S.A.*, 110: 4351-4356 (2013)). It was hypothesized that V3 clipping damages the variable loop-dependent structures at the trimer apex and that, accordingly, clipped trimers would flow through the column. It was further hypothesized that, because of the selectivity for PGT145 for native trimers, any non-native Env forms present (monomers, dimers, aggregates, uncleaved gp140s, etc.) would fail to bind to the PGT145 column, flow through, and be discarded.

Figure 20:
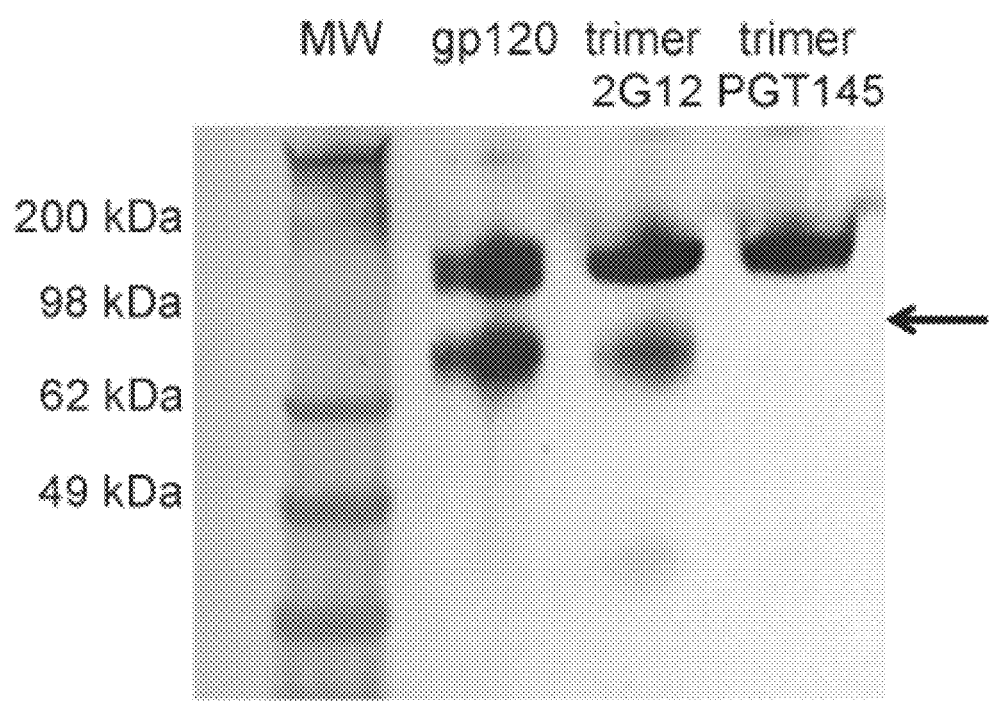
FIG. 20 is a blot that depicts the results of SDS-PAGE analysis of B41 gp120 monomers in comparison with B41 SOSIP.664 trimers. B41 gp120 monomers or SOSIP.664 trimers were produced in 293T cells in the 1121 presence of 10% serum, purified via either a 2G12 or a PGT145 affinity column and analyzed by reducing SDS-PAGE and western blotting with MAb ARP3119. The 70-kDa fragment of gp120 that is characteristic of V3-clipping is indicated with an arrow.
Figure 21:
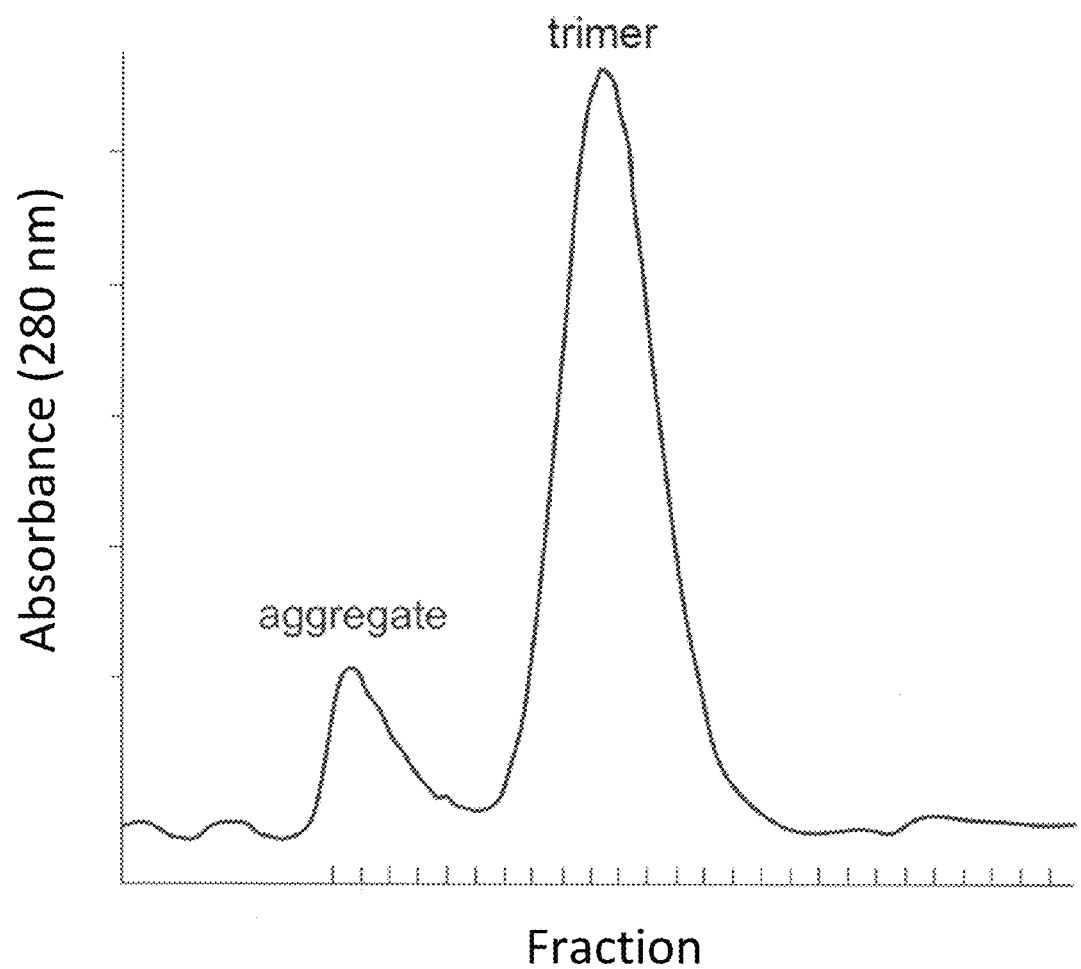
FIG. 21 is a graph that depicts the results of an analysis of B41 SOSIP.664 trimers purified using a PGT145 affinity column. The eluate from the column was analyzed by SEC on a Superdex 200 26/60 column. The X-axis represents fraction number and the Y-axis represents absorbance at 280 nm.

When B41 SOSIP.664 Env proteins were produced in 293T cells in the presence of 10% serum and then passed down the PGT145 column, the bound and then eluted trimers were not detectably V3-clipped, as shown in FIG. 20. This outcome contrasts with the purification of the same 293T cell-produced proteins via the 2G12 and SEC columns, which yielded trimers that were ~25% V3-clipped (see FIGS. 17, 20). Thus, by inference, V3-clipping does indeed destroy the PGT145 epitope at the trimer apex, allowing the use of the PGT145 column to positively select for non V3-clipped trimers. Moreover, PGT145 column-purified trimers were essentially homogeneous (i.e., free of contaminating Env aggregates, dimers or monomers) when analyzed by BN-PAGE or SEC, as shown in FIG. 21.

Figure 22:
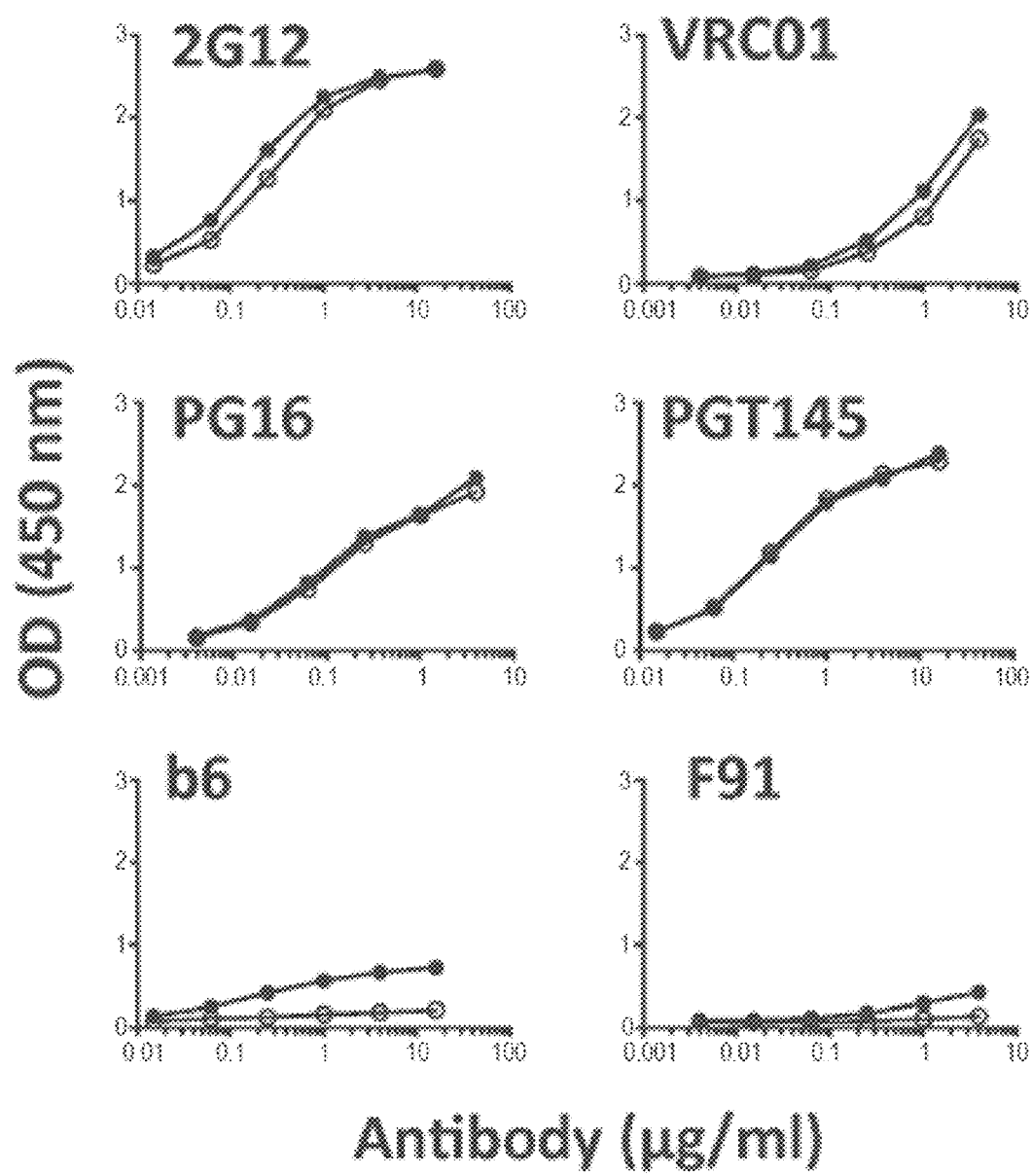
FIG. 22 provides representative binding curves of the indicated MAbs to B41 SOSIP.664-D7324 trimers purified either by the 2G12 affinity column followed by SEC (closed circles) or by the PGT145 affinity column (open circles). In both cases the trimers were produced in 293F cells in serum-free medium, and the extent of V3-clipping was <5%.

B41 SOSIP.664-D7324 trimers purified by the PGT145/SEC method were also analyzed by ELISA. Compared to non V3-clipped trimers purified by the 2G12/SEC method, 2G12, VRC01, PG16 and PGT145 each bound indistinguishably, whereas the binding of the non-NAbs b6 and F91 to their CD4bs epitopes was modestly reduced, as shown in FIG. 22. It is possible that the PGT145 column eliminates a very minor subset of non-native B41 trimers that is either present in preparations purified by the 2G12 and SEC method, or that arises over time.

The results of this example confirm that the use of the PGT145 column results in non V3-clipped homogenous trimers.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An expression vector comprising a first nucleic acid sequence encoding an HIV Env glycoprotein and a second nucleic acid sequence encoding a furin protease, wherein (i) expression of the nucleic acid sequence encoding the Env glycoprotein is controlled by a first constitutive promoter and the expression of the nucleic acid sequence encoding the furin protease is controlled by a second constitutive promoter, (ii) the first constitutive promoter is more potent than the second constitutive promoter, and (iii) the expression vector integrates into the genome of a mammalian cell.

2. The expression vector of claim 1, wherein the Env glycoprotein comprises a gp120 subunit and a gp41 subunit, wherein (i) the gp120 subunit and the gp41 subunit are linked by an inter-subunit disulfide bond, and (ii) the isoleucine at position 559 of the gp41 subunit is substituted with proline.

3. The expression vector of claim 1, wherein the Env glycoprotein forms the cleaved trimer BG505 SOSIP.664.

4. The expression vector of claim 1, wherein the Env glycoprotein forms the cleaved trimer B41 SOSIP.664.

5. The expression vector of claim 1, wherein the first constitutive promoter is a CMV promoter.

6. The expression vector of claim 1, wherein the second constitutive promoter is an EF1 alpha promoter.

7. The expression vector of claim 1, wherein the first nucleic acid sequence further comprises a synthetic poly A sequence.

8. The expression vector of claim 1, wherein the expression vector comprises a DNA plasmid.

9. The expression vector of claim 8, wherein the DNA plasmid comprises SEQ ID NO: 1.

10. The expression vector of claim 1, wherein the expression vector integrates into the genome of a mammalian cell via Flp-mediated recombination.

11. An isolated mammalian cell comprising the expression vector of claim 1.

12. The isolated mammalian cell of claim 11, which is a 293T cell.

13. The isolated mammalian cell of claim 11, which is a CHO cell.

14. A method of generating a mammalian cell line that expresses cleaved HIV Env glycoproteins, the method comprising:
  (a) transfecting one or more mammalian cells with the expression vector of claim 1 under conditions wherein the expression vector integrates into the genome of the one or more mammalian cells;
  (b) selecting one or more mammalian cells comprising the expression vector integrated into the genome thereof and expressing cleaved HIV Env glycoproteins; and
  (c) propagating the selected mammalian cells indefinitely, thereby generating a mammalian cell line that expresses cleaved HIV Env glycoproteins.

15. A method of producing cleaved Env glycoproteins, wherein the method comprises (i) culturing the isolated mammalian cell of claim 11 under conditions to express the first and second nucleic acid sequences to provide HIV Env glycoproteins and furin proteases, and (ii) allowing the furin protease to cleave the Env glycoproteins to provide cleaved Env glycoproteins.

16. The method of claim 15, which further comprises isolating and purifying the cleaved Env glycoproteins.

\* \* \* \* \*